US012378205B2

(12) United States Patent
Garg et al.

(10) Patent No.: US 12,378,205 B2
(45) Date of Patent: Aug. 5, 2025

(54) PROCESS FOR THE PREPARATION OF TRIAZINE INTERMEDIATES AND A PROCESS FOR THE PREPARATION OF UV ABSORBERS THEREOF

(71) Applicant: BASF SE, Ludwigshafen am Rhein (DE)

(72) Inventors: Rahul Garg, Navi Mumbai (IN); Prachin Kolambkar, Mumbai (IN); Mushtaq Patel, Navi Mumbai (IN)

(73) Assignee: BASF SE, Ludwigshafen am Rhein (DE)

( * ) Notice: Subject to any disclaimer, the term of this patent is extended or adjusted under 35 U.S.C. 154(b) by 992 days.

(21) Appl. No.: 17/421,301

(22) PCT Filed: Jan. 2, 2020

(86) PCT No.: PCT/EP2020/050005
§ 371 (c)(1),
(2) Date: Jul. 7, 2021

(87) PCT Pub. No.: WO2020/144093
PCT Pub. Date: Jul. 16, 2020

(65) Prior Publication Data
US 2022/0119357 A1    Apr. 21, 2022

(30) Foreign Application Priority Data
Jan. 8, 2019 (EP) .................................. 19150633

(51) Int. Cl.
*C07D 251/24* (2006.01)
(52) U.S. Cl.
CPC ................. *C07D 251/24* (2013.01)
(58) Field of Classification Search
CPC .................................................. C07D 251/24
See application file for complete search history.

(56) References Cited

U.S. PATENT DOCUMENTS 5,182,389 A * 1/1993 Burdeska ............. C07D 251/24
544/219
5,438,138 A    8/1995 Henneberger et al.

FOREIGN PATENT DOCUMENTS

EP    2762483 A1    8/2014

OTHER PUBLICATIONS

Brunetti, et al., "Die Synthese von asymmetrisch substituierten o-Hydroxyphenyl-s-triazinen", Helvetica Chimica Acta, vol. 55, Issue 5, Jul. 10, 1972, pp. 1566-1595.
European Search Report for EP Patent Application No. 19150633.6, Issued on Nov. 6, 2019, 4 pages.
International Search Report for PCT Patent Application No. PCT/EP2020/050005, Issued on Jun. 25, 2020, 5 pages.
Langmead, et al., "Identification of Novel Adenosine A2A Receptor Antagonists by Virtual Screening", Journal of Medicinal Chemistry, vol. 55, Issue 5, Jan. 17, 2012, pp. 1904-1909.
Pan, et al., "Base-Mediated Synthesis of Unsymmetrical 1,3,5-Triazin-2-amines via Three-Component Reaction of Imidates, Guanidines, and Amides or Aldehydes", The Journal of Organic Chemistry, vol. 82, Issue 19, Aug. 25, 2017, pp. 10043-10050.
Tanimoto, et al., "Synthesis of Ultraviolet Absorber Having 2-(2-Hydroxyphenyl)-1, 3, 5-Triazine Structure as a Functional Moiety", Senyo to Yakahin—Dyestuffs and Chemicals, vol. 40, Issue 12, Dec. 1995, pp. 325-339.

* cited by examiner

*Primary Examiner* — Timothy R Rozof
(74) *Attorney, Agent, or Firm* — ArentFox Schiff LLP

(57) ABSTRACT

The presently claimed invention relates to a novel, highly efficient and general process for the preparation of the triazine intermediates and their use in the preparation of UV absorbers.

15 Claims, No Drawings

PROCESS FOR THE PREPARATION OF TRIAZINE INTERMEDIATES AND A PROCESS FOR THE PREPARATION OF UV ABSORBERS THEREOF

CROSS-REFERENCE TO RELATED APPLICATIONS

This application is a National Stage Entry of PCT/EP2020/050005, filed Jan. 2, 2020, which claims priority to EP application No. 19150633.6, filed Jan. 8, 2019, the disclosures of each of which are hereby incorporated by reference in their entireties.

FIELD OF THE INVENTION

The presently claimed invention relates to a novel, highly efficient and general process for the preparation of the triazine intermediates and their use in the preparation of UV absorbers.

BACKGROUND OF THE INVENTION

Triazine UV absorbers are an important class of organic compounds which have a wide variety of applications. One of the most important areas of application is the protection and stabilization of organic materials such as plastics, polymers, coating materials, and photographic recording material against damages by light, heat, oxygen, or environmental forces. Other areas of applications include cosmetics, fibres, dyes, etc.

Triazine-derived UV absorbers are a class of compounds that typically include at least one 2-oxyaryl substituent on the 1,3,5-triazine ring. Triazine-based UV absorber compounds having aromatic substituents at the 2-, 4-, and 6-positions of the 1,3,5-triazine ring and having at least one of the aromatic rings substituted at the ortho position with a hydroxyl group or blocked hydroxyl group are generally the preferred compounds.

There are several processes known in the literature for the preparation of triazine-based UV absorbers. (See, H. Brunetti and C. E. Luethi, [0008] Helvetica Chimica Acta, 1972, 55, 1566-1595, S. Tanimoto et al., Senryo to Yakahin, 1995, 40(120), 325-339).

Langmead et.al. (Journal of Medicinal Chemistry, 2012, 1904-1909) and EP 2 762 483 A1 disclose use of Suzuki coupling to introduce the phenyl ring to a 2-amino triazines.

Many of the approaches consist of three stages. The first stage, the synthesis of the key intermediate, 2-chloro-4,6-bisaryl-1,3,5-triazine, from commercially available materials can involve single-step or multi-step processes. Thereafter, in the second stage, 2-chloro-4,6-bisaryl-1,3,5-triazine is subsequently arylated with 1,3-dihydroxybenzene (resorcinol) or a substituted 1,3-dihydroxybenzene in the presence of a Lewis acid to form the parent compound 2-(2,4-dihydroxyaryl)-4,6-bisaryl-1,3,5-triazine. The parent compound 2-(2,4-dihydroxyaryl)-4,6-bisaryl-1,3,5-triazine, as mentioned above, may be further functionalized, e.g., alkylated, to prepare a final product 2-(2-hydroxy-4-alkoxyaryl)-4,6-bisaryl-1,3,5-triazine.

There have been several approaches reported in the literature on the synthesis of the key intermediate 2-chloro-4,6-bisaryl-1,3,5-triazine. However, the problem associated with these approaches is that they lead to formation of impurities which are difficult to separate. The impurities react in the subsequent steps and will in turn lead to the formation of undesired products. Thus, there is a need for the preparation of 2-chloro-4,6-bisaryl-1,3,5-triazine without the formation of impurities or with minimal formation of these impurities.

SUMMARY OF THE INVENTION

Surprisingly, it was found that reacting 4,6-dichloro-1,3,5-triazin-2-amine with at least one aromatic compound in the presence of at least one acid allowed the formation 4,6-diaryl-1,3,5-triazin-2-amine, which can subsequently be converted to the desired UV absorber compounds.

Accordingly, the first aspect of the presently claimed invention is a process for preparing a compound of formula (A),

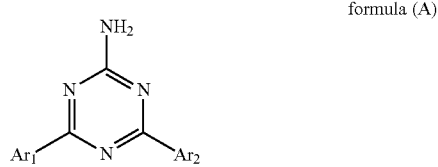

formula (A)

wherein $Ar_1$ and $Ar_2$ are independently a moiety of the formula (B),

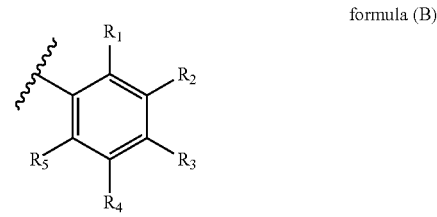

formula (B)

wherein
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and
R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of reacting at least one compound of formula (C)

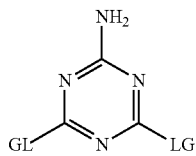

formula (C)

wherein LG is halogen, O—S(=O)$_2$CF$_3$ or O—S(=O)$_2$CH$_3$;
and at least one compound of formula (B2)

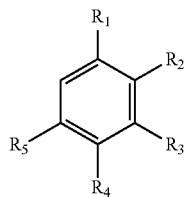

formula (B2)

wherein
R$_1$, R$_2$, R$_3$, R$_4$ and R$_5$ are independently selected from the group consisting of hydrogen, halogen, substituted or unsubstituted, linear or branched C$_1$-C$_{24}$ alkyl, substituted or unsubstituted, linear or branched C$_2$-C$_{24}$ alkenyl, substituted or unsubstituted C$_5$-C$_{24}$ cycloalkyl, substituted or unsubstituted C$_5$-C$_{24}$ cycloalkenyl, substituted or unsubstituted C$_6$-C$_{24}$ aryl, substituted or unsubstituted C$_7$-C$_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or R$_1$ and R$_2$ together with the carbon atoms to which they are bonded or R$_2$ and R$_3$ together with the carbon atoms to which they are bonded or R$_3$ and R$_4$ together with the carbon atoms to which they are bonded or R$_4$ and R$_5$ together with the carbon atoms to which they are bonded form an unsaturated or aromatic 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched C$_1$-C$_{24}$ alkyl, substituted or unsubstituted, linear or branched C$_2$-C$_{24}$ alkenyl, substituted or unsubstituted C$_5$-C$_{24}$ cycloalkyl, substituted or unsubstituted C$_5$-C$_{24}$ cycloalkenyl, substituted or unsubstituted C$_6$-C$_{24}$ aryl and substituted or unsubstituted C$_7$-C$_{24}$ arylalkyl; in the presence of at least one acid.

A second aspect of the presently claimed invention is a process for preparing a compound of formula (D),

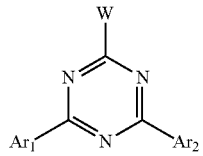

formula (D)

wherein Ar$_1$ and Ar$_2$ are defined as above, and
W is selected from the group consisting of F, Cl, and Br, comprising at least the steps of
i) reacting a compound of formula (A) obtained as described above with at least one diazotizing reagent to obtain a diazonium salt of formula (Aa),

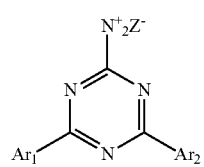

formula (Aa)

wherein Ar$_1$ and Ar$_2$ are as defined as above, and Z$^-$ is selected from the group consisting of BF$_4^-$, F$^-$, Cl$^-$ or Br$^-$; and
ii) reacting the diazonium salt of formula (Aa) obtained in step i) with at least one reagent of formula M(M$_a$)$_n$, wherein
M is selected from the group consisting of Cu, H and K,
M$_a$ is Cl, Br, I, BF$_4^-$ and
n is 1 to 4,
to obtain a compound of formula (D).

A third aspect of the presently claimed invention is a process for preparing a compound of formula (F),

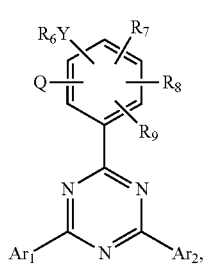

formula (F)

wherein Ar$_1$ and Ar$_2$ are the same or different and are as defined as above,
Q is selected from hydrogen or OH;
R$_6$ is selected from the group consisting of hydrogen, substituted or unsubstituted linear or branched C$_1$-C$_{24}$ alkyl, substituted or unsubstituted linear or branched C$_2$-C$_{24}$ alkenyl, substituted or unsubstituted C$_6$-C$_{24}$ aryl, substituted or unsubstituted C$_7$-C$_{24}$ arylalkyl, substituted or unsubstituted C$_5$-C$_{24}$ cycloalkyl, substituted or unsubstituted C$_5$-C$_{24}$ cycloalkenyl, and C(=O)R;
R$_7$, R$_8$ and R$_9$ are independently selected from the group consisting of hydrogen, halogen, substituted or unsubstituted linear or branched C$_1$-C$_{24}$ alkyl, substituted or unsubstituted linear or branched $C_2$-$C_{24}$alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is selected from the group consisting of hydrogen, halogen, O, —NR", or S, wherein R" is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present, comprising at least the steps of reacting at least one compound of formula (D)

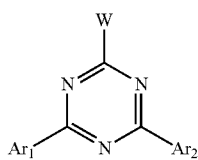

formula (D)

wherein W is halogen,
$Ar_1$ and $Ar_2$ are the same or different and are as defined as above,
and at least one compound of formula (E),

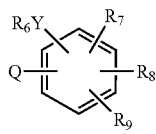

formula (E)

wherein
Q is selected from hydrogen and OH;
$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;
$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is selected from the group consisting of hydrogen, halogen, O, —NR", or S, wherein R" is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present, in the presence of an at least one acid.

DETAILED DESCRIPTION

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or 'a', 'b', 'c', etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein.

In case the terms 'first', 'second', 'third' or '(A)', '(B)' and '(C)' or '(a)', '(b)', '(c)', '(d)', 'i', 'ii' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

In an embodiment, the presently claimed invention is directed to a process for preparing a compound of formula (A):

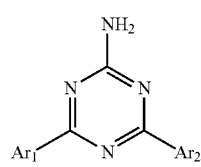

formula (A)

wherein $Ar_1$ and $Ar_2$ are independently a moiety of the formula (B),

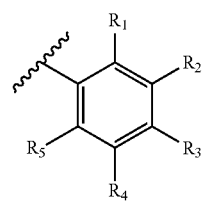

formula (B)

wherein
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and
R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;
comprising at least the steps of reacting at least one compound of formula (C)

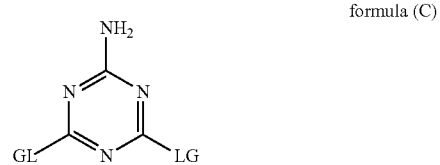

formula (C)

wherein LG is halogen, O—S(=O)$_2$CF$_3$ or O—S(=O)$_2$CH$_3$;
and at least one compound of formula (B2)

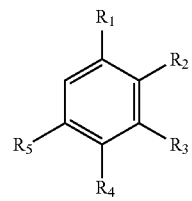

formula (B2)

wherein
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

in the presence of at least one acid.

More preferably, the presently claimed invention is directed to a process for preparing a compound of formula (A),

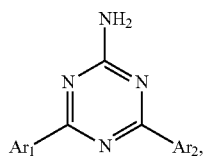

formula (A)

wherein $Ar_1$ and $Ar_2$ are independently a moiety of the formula (B),

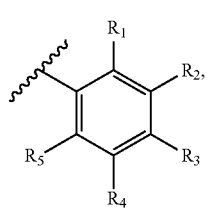

formula (B)

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of reacting at least one compound of formula (C),

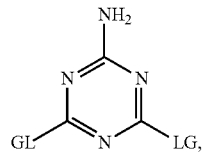

formula (C)

wherein LG is halogen, O—S(=O)$_2$CF$_3$ or O—S(=O)$_2$CH$_3$;

and at least one compound of formula (B1),

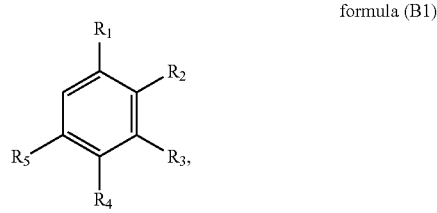

formula (B1)

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl;

in the presence of at least one acid.

Even more preferably, the presently claimed invention is directed to a process for preparing a compound of formula (A),

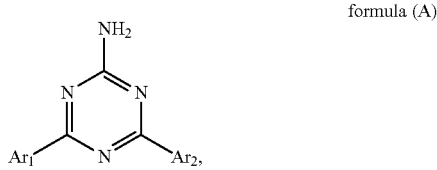

formula (A)

wherein $Ar_1$ and $Ar_2$ are independently a moiety of the formula (B),

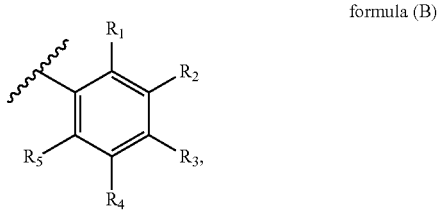

formula (B)

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_5$-$C_{24}$ cycloalkyl, substituted or unsubstituted $C_6$-$C_{24}$ aryl, substituted or unsubstituted $C_7$-$C_{24}$ arylalkyl, C(=O)R, OR, NRR' and C(=O)NRR'; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_6$-$C_{24}$ aryl and substituted or unsubstituted $C_7$-$C_{24}$ arylalkyl;

comprising at least the steps of reacting at least one compound of formula (C),

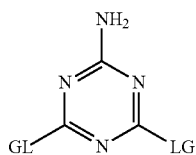

formula (C)

wherein LG is halogen;
and at least one compound of formula (B1),

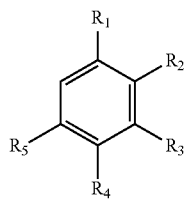

formula (B1)

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_5$-$C_{24}$ cycloalkyl, substituted or unsubstituted $C_6$-$C_{24}$ aryl, substituted or unsubstituted $C_7$-$C_{24}$ arylalkyl, C(=O)R, OR and NRR', C(=O)NRR'; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_6$-$C_{24}$ aryl and substituted or unsubstituted $C_7$-$C_{24}$ arylalkyl;

in the presence of at least one acid.

Most preferably, the presently claimed invention is directed to a process for preparing a compound of formula (A),

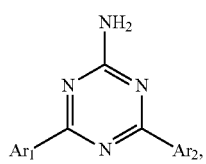

formula (A)

wherein $Ar_1$ and $Ar_2$ are independently a moiety of the formula (B),

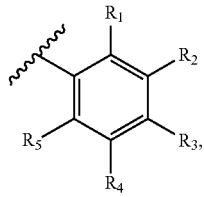

formula (B)

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, C(=O)R and OR; and R is independently selected from the group consisting of hydrogen, substituted or unsubstituted, linear or branched $C_1$-$C_{24}$ alkyl, substituted or unsubstituted $C_6$-$C_{24}$ aryl and substituted or unsubstituted $C_7$-$C_{24}$ arylalkyl;

comprising at least the steps of reacting at least one compound of formula (C),

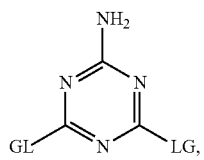

formula (C)

wherein LG is halogen;
and at least one compound of formula (B1),

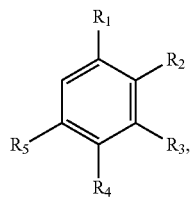

formula (B1)

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, C(=O)R and OR; and R is independently selected from the group consisting of hydrogen, substituted or unsubstituted, linear or branched $C_1$-$C_{24}$ alkyl, substituted or unsubstituted $C_6$-$C_{24}$ aryl and substituted or unsubstituted $C_7$-$C_{24}$ arylalkyl;

in the presence of at least one acid.

In particular, the presently claimed invention is directed to a process for preparing a compound of formula (A),

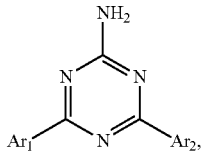

formula (A)

wherein $Ar_1$ and $Ar_2$ are independently a moiety of the formula (B),

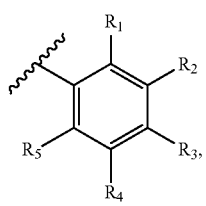

formula (B)

wherein
$R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, C(=O)R and OR; and
R is independently selected from the group consisting of hydrogen, substituted or unsubstituted, linear or branched $C_1$-$C_{24}$ alkyl, substituted or unsubstituted $C_5$-$C_{24}$ aryl and substituted or unsubstituted $C_7$-$C_{24}$ arylalkyl;
comprising at least the steps of reacting at least one compound of formula (C),

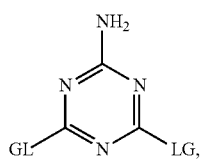

formula (C)

wherein LG is halogen;
and at least one compound of formula (B1),

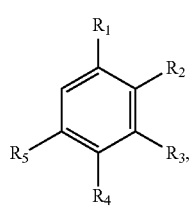

formula (B1)

wherein
$R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_5$-$C_{24}$ aryl, C(=O)R and OR; and R is independently selected from the group consisting of hydrogen, substituted or unsubstituted, linear or branched $C_1$-$C_{24}$ alkyl, substituted or unsubstituted $C_6$-$C_{24}$ aryl and substituted or unsubstituted $C_7$-$C_{24}$ arylalkyl;
in the presence of at least one Lewis acid.

Within the context of the presently claimed invention, the term "alkyl", as used herein, refers to an acylic saturated aliphatic group, including linear or branched alkyl saturated hydrocarbon radicals, denoted by a general formula $C_nH_{2n+1}$ and wherein n is the number of carbon atoms such as 1, 2, 3, 4, etc.

In a preferred embodiment, the unsubstituted linear $C_1$-$C_{24}$ alkyl is preferably selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl and tetracosyl; more preferably selected from the group consisting of hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl and tetracosyl; even more preferably selected from the group consisting of methyl, ethyl, propyl, butyl, pentyl, hexyl, heptyl, octyl, nonyl, decyl, undecyl, dodecyl, tridecyl, tetradecyl and pentadecyl; most preferably selected from the group consisting of methyl, ethyl, propyl, butyl, pentyl, hexyl, heptyl, octyl, nonyl, decyl, undecyl and dodecyl; and in particular preferably selected from the group consisting of methyl, ethyl, propyl, butyl, pentyl, hexyl, heptyl, octyl, nonyl and decyl.

In a preferred embodiment, the unsubstituted branched $C_1$-$C_{24}$ alkyl is preferably selected from the group consisting of isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl, more preferably selected from the group consisting of 2-ethyl-hexyl, 2-propyl-heptyl, 2-butyl-octyl, 2-pentyl-nonyl, 2-hexyl-decyl, isohexyl, iso-heptyl, iso-octyl, iso-nonyl, iso-decyl, iso-dodecyl, iso-tetradecyl, iso-hexadecyl, iso-octadecyl, iso-eicosyl, 2methyl tricosyl, 2 ethyl docosyl, 3 ethylhenicosyl, 3-ethyl icosyl, 4-propylhenicosyl, propyinonadecyl, 6-butyldodecyl and 5-ethylundedcyl.

In a preferred embodiment, the substituted, linear or branched, $C_1$-$C_{24}$ alkyl refers to a branched or linear saturated hydrocarbon group having $C_1$-$C_{24}$ carbon atoms substituted with functional groups selected from the group consisting of hydroxy, alkoxy, C(=O)R, CN and SR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

In a preferred embodiment, the substituted, linear or branched, $C_1$-$C_{24}$ alkyl refers to a branched or linear saturated hydrocarbon group having $C_1$-$C_{24}$ carbon atoms substituted with functional groups selected from the group consisting of hydroxy, alkoxy, C(=O)R, CN and SR, preferably selected from the group consisting of 1-hydroxy methyl, 1-methoxy methyl, 1-hydroxy ethyl, 1-hydroxy propyl, 1-hydroxy butyl, 1-hydroxy pentyl, 1-hydroxy hexyl, 1-hydroxy heptyl, 1-hydroxy octyl, 1-hydroxy nonyl, decyl, 1-hydroxy undecyl, 1-hydroxy dodecyl, 1-hydroxy tridecyl, 1-hydroxy tetradecyl, 1-hydroxy pentadecyl, 1-hydroxy hexadecyl, 1-hydroxy heptadecyl, 1-hydroxy octadecyl, 1-hydroxy nonadecyl, 1-hydroxy eicosyl, 1-hydroxy henicosyl, 1-hydroxy docosyl, 1-hydroxy tricosyl, 1-hydroxy tetracosyl, 1-methoxy methyl, 1-methoxy ethyl, 1-methoxy propyl, 1-methoxy butyl, 1-methoxy pentyl, 1-methoxy hexyl, 1-methoxy heptyl, 1-methoxyoctyl, 1-methoxy nonyl, decyl, 1-methoxy undecyl, 1-methoxy dodecyl, 1-methoxy tridecyl, 1-methoxy tetradecyl, 1-methoxy pentadecyl, 1-methoxy hexadecyl, 1-methoxy heptadecyl, 1-methoxy octadecyl, 1-methoxy nonadecyl, 1-methoxy eicosyl, 1-methoxy henicosyl, 1-methoxy docosyl, 1-methoxy tricosyl, 1-methoxy tetracosyl, 2-methoxy propyl, 2-methoxy butyl, 2-methoxy pentyl, 2-methoxy hexyl, 2-methoxy heptyl, 2-methoxy octyl, 2-methoxy nonyl, decyl, 2-methoxy undecyl, 2-methoxy dodecyl, 2-methoxy tridecyl, 2-methoxy tetradecyl, 2-methoxy pentadecyl, 2-methoxy hexadecyl, 2-methoxy heptadecyl, 2-methoxy octadecyl, 2-methoxy nonadecyl, 2-methoxy eicosyl, 2-methoxy henicosyl, 2-methoxy docosyl, 2-methoxy tricosyl, 2-methoxy tetracosyl, 1-acetoxy methyl, 1-acetoxy ethyl, 1-acetoxy propyl, 1-acetoxy butyl, 1-acetoxy pentyl, 1-acetoxy hexyl, 1-acetoxy heptyl, 1-acetoxy octyl, 1-acetoxy nonyl, decyl, 1-acetoxy undecyl, 1-acetoxy dodecyl, 1-acetoxy tridecyl, 1-acetoxy tetradecyl, 1-acetoxy pentadecyl, 1-acetoxy hexadecyl, 1-acetoxy heptadecyl, 1-acetoxy octadecyl, 1-acetoxy nonadecyl, 1-acetoxy eicosyl, 1-acetoxy henicosyl, 1-acetoxy docosyl, 1-acetoxy tricosyl, 1-acetoxy tetracosyl, 1-cyano methyl, 1-cyano ethyl, 1-cyano propyl, 1-cyano butyl, 1-cyano pentyl, 1-cyano hexyl, 1-cyano heptyl, 1-cyano octyl, 1-cyano nonyl, decyl, 1-cyano undecyl, 1-cyano dodecyl, 1-cyano tridecyl, 1-cyano tetradecyl, 1-cyano pentadecyl, 1-cyano hexadecyl, 1-cyano heptadecyl, 1-cyano octadecyl, 1-cyano nonadecyl, 1-cyano eicosyl, 1-cyano henicosyl, 1-cyano docosyl, 1-cyano tricosyl, 1-cyano tetracosyl, 2-cyano propyl, 2-cyano butyl, 2-cyano pentyl, 2-cyano hexyl, 2-cyano heptyl, 2-cyano octyl, 2-cyano nonyl, decyl, 2-cyano undecyl, 2-cyano dodecyl, 2-cyano tridecyl, 2-cyano tetradecyl, 2-cyano pentadecyl, 2-cyano hexadecyl, 2-cyano heptadecyl, 2-cyano octadecyl, 2-cyano nonadecyl, 2-cyano eicosyl, 2-cyano henicosyl, 2-cyano docosyl, 2-cyano tricosyl, 2-cyano tetracosyl, 1-thioyl methyl, 1-thioyl ethyl, 1-thioyl propyl, 1-thioyl butyl, 1-thioyl pentyl, 1-thioyl hexyl, 1-thioyl heptyl, 1-thioyl octyl, 1-thioyl nonyl, decyl, 1-thioyl undecyl, 1-thioyl dodecyl, 1-thioyl tridecyl, 1-thioyl tetradecyl, 1-thioyl pentadecyl, 1-thioyl hexadecyl, 1-thioyl heptadecyl, 1-thioyl octadecyl, 1-thioyl nonadecyl, 1-thioyl eicosyl, 1-thioyl henicosyl, 1-thioyl docosyl, 1-thioyl tricosyl and 1-thioyl tetracosyl.

In a preferred embodiment, the term alkenyl denotes unsubstituted linear $C_2$-$C_{24}$ alkenyl which is preferably selected from the group consisting of 1-propenyl, 1-butenyl, 1-pentenyl, 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, more preferably selected from 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, 20-henicosenyl, 2-docosenyl, 6-tricosenyl and 2-tetracosenyl.

In a preferred embodiment, the unsubstituted branched $C_2$-$C_{24}$alkenyl is selected from the group consisting of isopropenyl, iso-butenyl, neo-pentenyl, 2-ethyl-hexenyl, 2-propyl-heptenyl, 2-butyloctenyl, 2-pentyl-nonenyl, 2-hexyl-decenyl, iso-hexenyl, iso-heptenyl, iso-octenyl, iso-nonenyl, iso-decenyl, iso-dodecenyl, iso-tetradecenyl, iso-hexadecenyl, iso-octadecenyl, iso-eicosenyl, 2-methyl tricosenyl, 2-ethyl docosenyl, 3-ethylhenicosenyl, 3-ethyl icosenyl, 4-propylhenicosenyl, 4-propylnonadecenyl, 6-butyldodecenyl, 5-ethylundedcenyl, 1,4-hexadienyl, 1,3-hexadienyl, 2,5-hexadienyl, 3,5-hexadienyl, 2,4-hexadienyl, 1,3,5-hexatrienyl, 1,3,6-heptatrienyl, 1,4,7-octatrienyl or 2-methyl-1,3,5hexatrienyl, 1,3,5,7-octatetraenyl, 1,3,5,8-nonatetraenyl, 1,4,7,10-undecatetraenyl, 2-ethyl-1,3,6,8-nonatetraenyl, 2-ethenyl-1,3,5,8-nonatetraenyl, 1,3,5,7,9-decapentaenyl, 1,4,6,8,10-undecapentaenyl, and 1,4,6,9,11-dodecapentaenyl.

In a preferred embodiment, the substituted, linear or branched, $C_2$-$C_{24}$ alkenyl refers to a branched or an linear unsaturated hydrocarbon group having $C_2$-$C_{24}$ carbon atoms substituted with functional groups selected from, hydroxy, alkoxy, C(=O)R, CN and SR; wherein R is hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl.

In a preferred embodiment the substituted, linear or branched, $C_2$-$C_{24}$ alkenyl refers to a branched or an linear unsaturated hydrocarbon group having $C_2$-$C_{24}$ carbon atoms substituted with functional groups selected from, hydroxy, alkoxy, C(=O)R, CN and SR; preferably selected from the group consisting of 2-hydroxy propenyl, 3-hydroxy butenyl, 3-hydroxy pentenyl, 5-hydroxy hexenyl, 7-hydroxy heptenyl, 3-hydroxy octenyl, 5-hydroxy nonenyl, decyl, 11-hydroxy undecenyl, 9-hydroxy dodecenyl, 6-hydroxy tridecenyl, 4-hydroxy tetradecenyl, 6-hydroxy pentadecenyl, 3-hydroxy hexadecenyl, 2-hydroxy heptadecenyl, 7-hydroxy octadecenyl, 6-hydroxy nonadecenyl, 4-hydroxy eicosenyl, 2-hydroxy henicosenyl, 3-hydroxy docosenyl, 2-hydroxy tricosenyl, 23-hydroxy tetracosenyl, 1-methoxy ethenyl, 2-methoxy propenyl, 4-methoxy butenyl, 3-methoxy pentenyl, 5-methoxy hexenyl, 2-methoxy heptenyl, 5-methoxy octenyl, 3-methoxy nonenyl, 6-methoxy undecenyl, 1-methoxy dodec-2-enyl, 1-methoxy tridec-5-enyl, 3-methoxy tetradic-5-enyl, 3-methoxy pentade-12-encyl, 10-methoxy hexadec-15-enyl, 12-methoxy heptadic-16-enyl, 1-methoxy octadec-3-enyl, 1-methoxy nonadec-2-enyl, 1-methoxy eicos-20-enyl, 1-methoxy henicos-2-enyl, 1-methoxy docos-4-enyl, 1-methoxy tricos-22-enyl, 1-methoxy tetracos-23-enyl, 2-methoxy prop-1-enyl, 2-methoxy but-1-enyl, 2-methoxy pent-4-enyl, 2-methoxy hex-2-enyl, 2-methoxy hept-3-enyl, 2-methoxy oct-7-enyl, 2-methoxy non-5-enyl, 2-methoxy undec-10-enyl, 2-methoxy dodec-4-enyl, 2-methoxy tridec-12-enyl, 2-methoxy tetradic-10-enyl, 2-methoxy pentadec-14-enyl, 2-methoxy hexadec-1-enyl, 2-methoxy heptadic-1-enyl, 2-methoxy octadic-12-enyl, 2-methoxy nonadec-10-enyl, 2-methoxy eicos-18-enyl, 2-methoxy henicos-2-enyl, 2-methoxy docos-3-enyl, 20-methoxy tricos-2-enyl, 21-methoxy tetracos-4-enyl, 1-acetoxy ethenyl, 1-acetoxy prop-1-enyl, 1-acetoxy but-2-enyl, 1-acetoxy pent-4-enyl, 1-acetoxy hex-2-enyl, 1-acetoxy hept-1-enyl, 1-acetoxy oct- 7-enyl, 1-acetoxy non-2-enyl, 5-acetoxy dec-3-enyl, 1-acetoxy undec-10-enyl, 1-acetoxy dodec-2-enyl, 1-acetoxy tridec-12-enyl, 10-acetoxy tetradec-2-enyl, 15-acetoxy pentadec-2-enyl, 10-acetoxy hexadec-2-enyl, 11-acetoxy heptadec-1-enyl, 13-acetoxy octadec-2-enyl, 1-acetoxy nonadec-14-enyl, 20-acetoxy eicos-19-enyl, 1-acetoxy henicos-2-enyl, 1-acetoxy docos-10-enyl, 1-acetoxy tricos-22-enyl, 1-acetoxy tetracos-23-enyl, 1-cyano eth-1-enyl, 1-cyano prop-2-enyl, 1-cyano but-2-enyl, 1-cyano pent-3-enyl, 1-cyano hex-5-enyl, 1-cyano hept-6-enyl, 1-cyano oct-2-enyl, 1-cyano non-3-enyl, 11-cyano undec-2-enyl, 10-cyano dodec-2-enyl, 10-cyano tridec-12-enyl, 1-cyano tetradec-3-enyl, 1-cyano pentadec-14-enyl, 1-cyano hexadec-15-enyl, 1-cyano heptadec-2-enyl, 1-cyano octadec-3-enyl, 1-cyano nonadec-18-enyl, 1-cyano eicos-10-enyl, 1-cyano henicos-20-enyl, 15-cyano docos-3-enyl, 1-cyano tricos-20-enyl, 1-cyano tetracos-2-enyl, 2-cyano prop-2-enyl, 2-cyano but-1-enyl, 2-cyano pent-1-enyl, 2-cyano hex-3-enyl, 2-cyano hept-6-enyl, 2-cyano oct-1-enyl, 2-cyano non-8-enyl, 2-cyano undec-10-enyl, 2-cyano dodec-1-enyl, 2-cyano tridec-12-enyl, 2-cyano tetradec-10-enyl, 2-cyano pentadec-3-enyl, 2-cyano hexadec-2-enyl, 2-cyano heptadec-1-enyl, 2-cyano octadec-12-enyl, 2-cyano nonadec-15-enyl, 2-cyano eicos-1-enyl, 2-cyano henicos-5-enyl, 2-cyano docos-20-enyl, 2-cyano tricos-22-enyl, 2-cyano tetracos-20-enyl, 1-thionyl eth-1-enyl, 1-thionyl prop-2-enyl, 1-thionyl but-2-enyl, 1-thionyl pent-4-enyl, 1-thionyl hex-2-enyl, 1-thionyl hept-5-enyl, 1-thionyl oct-3-enyl, 1-thionyl non-5-enyl, 1-thionyl undec-10-enyl, 1-thionyl dodec-11-enyl, 1-thionyl tridec-2-enyl, 1-thionyl tetradec-4-enyl, 1-thionyl pentadec-5-enyl, 1-thionyl hexadec-3-enyl, 1-thionyl heptadec-2-enyl, 1-thionyl octadec-3-enyl, 1-thionyl nonadec-15-enyl, 1-thionyl eicos-18-enyl, 1-thionyl henicos-20-enyl, 1-thionyl docos-21-enyl, 1-thionyl tricos-20-enyl and 1-thionyl tetracos-22-enyl.

In a preferred embodiment, the substituted or unsubstituted $C_5$-$C_{24}$ cycloalkyl refers to a monocyclic and bicyclic 5 to 24 membered saturated cycloaliphatic radical. Representative examples of unsubstituted or branched $C_5$-$C_{24}$ monocyclic and bicyclic cycloalkyl include, but are not limited to, cyclopentyl, cyclohexyl, cycloheptyl, cyclooctyl, bicyclo[2.2.1]heptyl, and bicyclo[3.1.1]heptyl.

In another preferred embodiment, the $C_5$-$C_{24}$ monocyclic and bicyclic cycloalkyl can be further branched with one or more equal or different alkyl groups such as methyl, ethyl, n-propyl, isopropyl, n-butyl, iso-butyl, n-pentyl, iso-pentyl, neo-pentyl etc. The representative examples of branched $C_3$-$C_{10}$ monocyclic and bicyclic cycloalkyl include, but are not limited to, methyl cyclohexyl and dimethyl cyclohexyl.

In a preferred embodiment, the unsubstituted or branched $C_5$-$C_{24}$ cycloalkenyl refers to a monocyclic and bicyclic 5 to 24 membered unsaturated cycloaliphatic radical, which comprises one or more double bonds. Representative examples of $C_5$-$C_{24}$ cycloalkenyl include, but are not limited to, cyclopentenyl, cyclohexenyl, cycloheptenyl, cyclooctenyl, cyclononenyl or cyclodecenyl.

These radicals can be branched with one or more equal or different alkyl radical, preferably with methyl, ethyl, n-propyl or iso-propyl. The representative examples of branched $C_5$-$C_{24}$ monocyclic and bicyclic cycloalkenyl include, but not limited to methyl cyclohexenyl and dimethyl cyclohexenyl.

In a preferred embodiment, the unsubstituted $C_6$-$C_{24}$ aryl may have more than one aromatic ring.

The representative examples for substituted and unsubstituted $C_6$-$C_{24}$ aryl include, phenyl, naphthyl, anthracenyl, tetraphenyl, phenalenyl and phenanthrenyl.

In a preferred embodiment, the arylalkyl, refers to an aryl ring attached to an alkyl chain. The representative examples for the arylalkyl includes, but are not limited to, 1-phenylmethyl, 1-phenylethyl, 1-phenylpropyl, 1-phenylbutyl, 1-methyl-1-phenyl-propyl, 3-phenylpropyl, 4-phenylbutyl, 3-phenylbutyl and 2-methyl-3-phenyl-propyl.

In a preferred embodiment, the substituted $C_6$-$C_{24}$ aryl refers to an aromatic ring having substitution at different positions. The $C_6$-$C_{24}$ aryl may have more than one aromatic ring. The representative examples for substituted and unsubstituted $C_6$-$C_{24}$ aryl include tolyl, xylyl, 2-hydroxyphenyl, 2,3-dihydroxyphenyl, 2-methoxy phenyl, 2-hydroxy-4-methoxyphenyl, -2,4-dimethoxyphenyl, 2-chlorophenyl, 2-chloro-4-hydroxyphenyl, 2-chloro-4-methoxy phenyl, 3-chloro-4-methoxyphenyl, 2-methyl-4-methoxy-6-chlorophenyl and 2-acetyl-4-hydroxyphenyl.

In a preferred embodiment, the $R_1$, $R_2$, $R_3$, $R_4$ and $R_5$ are independently C(=O)R. The representative example include C(=O)CH$_3$, C(=O)C$_2$H$_5$, C(=O)C$_3$H$_7$, C(=O)C$_4$H$_9$, C(=O)C$_4$H$_7$, C(=O)C$_6$H$_{11}$, C(=O)C$_6$H$_9$, C(=O)C$_9$H$_{19}$, C(=O)C$_{10}$H$_{19}$, C(=O)C$_{10}$H$_{21}$, C(=O)C$_{15}$H$_{31}$, C(=O)C$_{13}$H$_{27}$, C(=O)C$_{14}$H$_{29}$, C(=O)C$_{15}$H$_{31}$ and C(=O)C$_{20}$H$_{41}$.

In a preferred embodiment, the $R_1$, $R_2$, $R_3$, $R_4$ and $R_5$ are independently OR. The representative example include OCH$_3$, OC$_2$H$_5$, OC$_3$H$_7$, OC$_4$H$_9$, OC$_4$H$_7$, OC$_5$H$_{11}$, OC$_6$H$_{11}$, OCSH$_9$, OC$_7$H$_{15}$, OCaH$_{17}$, OC$_9$H$_{19}$, OC$_{10}$H$_{19}$, OC$_{10}$H$_{21}$, OC$_{15}$H$_{31}$, OC$_{13}$H$_{27}$, OC$_{14}$H$_{29}$, OC$_{15}$H$_{31}$ and OC$_{20}$H$_{41}$.

In a preferred embodiment, the $R_1$, $R_2$, $R_3$, $R_4$ and $R_5$ are independently NRR', wherein R and R' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neopentyl, 2-ethyl-hexyl, 2-propyl-heptyl, 2-butyl-octyl, 2-pentyl-nonyl, 2-hexyl-decyl, iso-hexyl, isoheptyl, iso-octyl, iso-nonyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and $R_5$ are independently C(=O)NRR', wherein R and R' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, isobutyl, neo-pentyl, 2-ethyl-hexyl, 2-propyl-heptyl, 2-butyl-octyl, 2-pentyl-nonyl, 2-hexyl-decyl, isohexyl, iso-heptyl, iso-octyl, iso-nonyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and $R_5$ are independently SR, wherein R is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, isohexyl, iso-heptyl, iso-octyl, isononyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and $R_5$ are independently S(=O)$_2$R, wherein R is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethylhexyl, 2-propylheptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl.

In another preferred embodiment, the alkali metals are selected from the group consisting of lithium, sodium, potassium, caesium, magnesium, beryllium, barium, strontium, more preferably selected from the group consisting of lithium, sodium, potassium and caesium, most preferably selected from the group consisting of sodium and potassium.

In another preferred embodiment, the at least one compound of formula (C) is

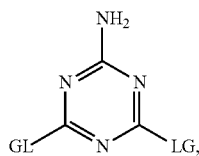

formula (C)

wherein LG is halogen, $OSO_2CF_3$ or $OSO_2CH_3$.

The representative examples for compounds of formula (C) are 4,6-dichloro-1,3,5-triazin-2-amine, 4,6-dibromo-1,3,5-triazin-2-amine, 4,6-diiodo-1,3,5-triazin-2-amine, 6-amino-1,3,5-triazine-2,4-diyl dimethanesulfonate, and 6-amino-1,3,5-triazine-2,4-diyl bis(trifluoromethanesulfonate).

The representative example for the at least one compound of formula (B2) include benzene, toluene, xylene, cresol, biphenyl, 2,3-dimethylphenol, 2-methylbenzene-1,3-diol, 3-(methoxy)-2-methylphenol, 3-(ethoxy)-2-methylphenol, 3-(propoxy)-2-methylphenol, 3-(butoxy)-2-methylphenol, 3-(pentoxy)-2-methylphenol, 3-(hexyloxy)-2-methylphenol, 3-((2-ethylhexyl)oxy)-2-methylphenol, 3-((2-ethylhexyl)oxy)phenol, 3-(hexyloxy)phenol, 1,3-bis(methoxy)benzene, 1,3-bis(ethoxy)benzene, 1,3-bis(propoxy)benzene, 1,3-bis(butoxy)benzene, 1,3-bis(pentoxy)benzene and 1,3-bis(hexoxy)benzene.

In another preferred embodiment, the at least one acid is selected from the group consisting of inorganic acid, Lewis acid, and organic acid.

In another preferred embodiment, the at least one inorganic acid is selected from the group consisting of sulfuric acid, hydrochloric acid, phosphoric acid ($H_3PO_4$), phosphorous acid ($H_3PO_3$), phosphinic acid ($H_3PO_2$), perchloric acid, nitric acid, nitrous acid, sulphurous acid, chloric acid, chlorous acid and hypochlorous acid; more preferably the at least one inorganic acid is hydrochloric acid.

In another preferred embodiment, the at least one Lewis acid is selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), Zr(acetylacetonate)$_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, $Ag(acetate)$, $Tl(acetate)_3$, Sc(trifluoromethanesulfonate)$_3$, Ln(trifluoromethanesulfonate)$_3$, Ni(trifluoromethanesulfonate)$_2$, $Ni(tosylate)_2$, Co(trifluoromethanesulfonate)$_2$, $Co(tosylate)_2$, Cu(tri-fluoromethanesulfonate)$_2$ and $Cu(tosylate)_2$; more preferably the Lewis acid is selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; most preferably selected from the group consisting of $BX_3$, $BX_3$—$(C_2H_5)_2O$, $BX_3$—$S(CH_3)_2$, $AlX_3$, $(C_2H_5)_2AlX$, $TiX_2$, $TiX_4$ whereby X in each case denotes F, Cl, Br, $S(=O)_3$, $CF_3$—$S(=O)_2O$, $CH_3$—$S(=O)_2O$, or I; particularly preferably, selected from the group consisting of $BX_3$, $AlX_3$, $(C_2H_5)_2AlX$, whereby X in each case denotes F, Cl, Br, $CF_3$—$S(=O)_2O$, $CH_3$—$S(=O)_2O$, or I.

In another preferred embodiment, the at least one Lewis acid is selected from the group consisting of $BX_3$, $BX_3$—$(C_2H_5)_2O$, $BX_3$—$S(CH_3)_2$, $AlX_3$, $ZnX_2$, $FeX_3$ and $TiX_4$, whereby X in each case denotes F, Cl, or Br.

In another preferred embodiment, the at least one organic acid is selected from the group consisting organic carboxylic acid and organic sulfonic acid.

In another preferred embodiment, the at least one organic carboxylic acid is selected from the group consisting of acetic acid, formic acid, propionic acid, butanoic acid, benzoic acid, phthalic acid, oxalic acid, malonic acid, succinic acid, glutaric acid, adipic acid, lactic acid, citric acid, uric acid and malic acid; more preferably the at least one organic carboxylic acid is selected from the group consisting of acetic acid, formic acid, propionic acid, butanoic acid and benzoic acid; most preferably the at least one organic carboxylic acid is selected from the group consisting of acetic acid and formic acid.

In a preferred embodiment, the organic sulfonic acid is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid, more preferably the organic sulfonic acid is selected from the group consisting of methanesulfonic acid, trifluoromethanesulfonic acid, benzenesulfonic acid and p-toluenesulfonic acid, even more preferably the organic sulfonic acid is selected from the group consisting of methanesulfonic acid and p-toluenesulfonic acid.

In another preferred embodiment, the molar ratio of the at least one acid to the at least one compound of formula (C) is in the range of 1:10 to 10:1, more preferably in the range of 1:5 to 5:1, most preferably in the range of 1:2 to 2:1.

In another preferred embodiment, the molar ratio of the at least one compound of formula (B2) to the at least one compound of formula (C) is in the range of 1:1.0 to 5:2.0, more preferably in the range of 1:2 to 3:2 and most preferably in the range of 1:2 to 2:1.

In another preferred embodiment, the at least one compound of formula (C) and the at least one compound of formula (B2) are reacted in the presence of at least one solvent selected from the group consisting of aliphatic hydrocarbons, aromatic hydrocarbons, aliphatic acyclic ether, aliphatic cyclic ether and carbon disulfide.

In another preferred embodiment the aliphatic hydrocarbons are selected from the group consisting of nitroalkanes, heptane, cyclohexane, dichloromethane, chloroform, carbon tetrachloride, dibromomethane, bromoform, iodomethane, diiodomethane, dichloroethane, 1,1,2,2-tetrachloroethane, acetone, acetic acid, hexane; more preferably the aliphatic hydrocarbons are selected from the group consisting of dichloroethane, 1,1,2,2-tetrachloroethane, dimethylsulfoxide and tetramethylene sulfone.

In another preferred embodiment the aromatic hydrocarbons are selected from the group consisting of benzene, toluene, xylene, nitrobenzene, dinitrobenzene, chlorobenzene, dichlorobenzene, trichlorobenzene, fluorobenzene, difluoro benzene, trifluoro benzene, bromobenzene, dibromo benzene, tribromo benzene; more preferably the aromatic hydrocarbons are selected from the group consisting of benzene, nitrobenzene, dinitrobenzene, and toluene In another preferred embodiment, the aliphatic acyclic ether and the aliphatic cyclic ether are selected from the group consisting of di tert-butyl ether, dioxane and tetrahydrofuran.

In another preferred embodiment, the molar concentration of the at least one compound of formula (C) in the at least one solvent is in the range of 0.5 M to 8.0 M, more preferably is in the range of 1.0 M to 6.0 M, even more preferably is in the range of 1.0 M to 5.0 M, most preferably is in the range of 1.0 M to 3.0 M, and in particular preferably is in the range of 1.0 M to 2.0 M.

In another preferred embodiment, the molar concentration of the at least one compound of formula (82) in the at least one solvent is in the range of 0.5 M to 8.0 M, more preferably is in the range of 1.0 M to 6.0 M, even more preferably is in the range of 1.0 M to 5.0 M, most preferably is in the range of 1.0 M to 3.0 M, and in particular preferably is in the range of 1.0 M to 2.0 M.

In another preferred embodiment, the at least one compound of formula (C) and the at least one compound of formula (B2) are reacted at a temperature in the range of 0° C. to 250° C., more preferably in the temperature in the range of 30° C. to 200° C., most preferably temperature in the range of 50° C. to 150° C. and in particular preferably temperature in the range of 80° C. to 120° C. In a preferred embodiment, the at least one compound of formula (C) and the at least one compound of formula (B2) are reacted for a period in the range of 30 minutes to 24 hours, more preferably reacted for a period in the range of 30 minutes to 15 hours, most preferably reacted for a period in the range of 1 minutes to 10 hours and in particular preferably reacted for a period in the range of 1 minutes to 5 hours.

The compound of formula (A) formed in the reaction is isolated by any method known in the art selected from the group consisting of chemical separation, acid-base neutralization, distillation, evaporation, column chromatography, filtration, concentration, crystallization and re-crystallization or a combination thereof. A person skilled in the art is aware of such techniques.

In an embodiment, the presently claimed invention is directed to a process for preparing a compound of formula (D),

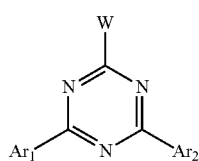

formula (D)

wherein $Ar_1$ and $Ar_2$ are defined as above, and
W is selected from the group consisting of F, Cl, and Br, comprising at least the steps of
i) reacting a compound of formula (A) with at least one diazotizing reagent to obtain a diazonium salt of formula (Aa);

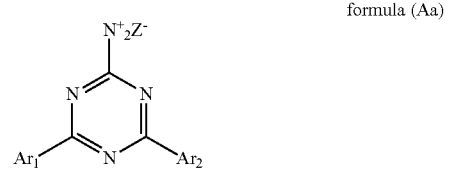

formula (Aa)

wherein $Ar_1$ and $Ar_2$ are as defined as above, and $Z^-$ is selected from the group consisting of $BF_4^-$, $F^-$, $Cl^-$ or $Br^-$; and
ii) reacting the diazonium salt of formula (Aa) obtained in step i) with at least one reagent of formula $M(M_a)_n$, wherein
M is selected from the group consisting of, Cu, H, K
$M_a$ is Cl, Br, I, $BF_4^-$ and
n is 1 to 4,
to obtain a compound of formula (D).

More preferably the presently claimed invention is directed to a process for preparing a compound of formula (D),

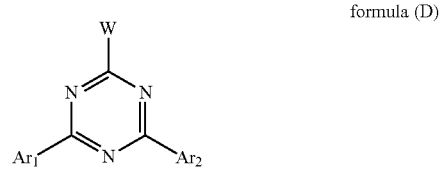

formula (D)

wherein $Ar_1$ and $Ar_2$ are defined as above, and
W is Cl,
comprising at least the steps of
i) reacting a compound of formula (A) with at least one diazotizing reagent to obtain a diazonium salt of formula (Aa);

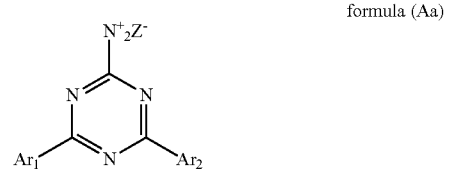

formula (Aa)

wherein $Ar_1$ and $Ar_2$ are as defined as above, and $Z^-$ is selected from the group consisting of $BF_4^-$, $F^-$, $Cl^-$ or $Br^-$; and
ii) reacting the diazonium salt of formula (Aa) obtained in step i) with at least one reagent of formula $M(M_a)_n$, wherein
M is selected from the group consisting of, Cu, H, K
$M_a$ is Cl, Br, I, $BF_4^-$ and
n is 1 to 4,
to obtain a compound of formula (D).

In a preferred embodiment, the compound of formula (A) is selected from the group consisting of 2-(4-amino-6-(2,4- dipropoxyphenyl)-1,3,5-triazin-2-yl)-5-propoxyphenol, 2-(4-amino-6-(2,4-dipropoxyphenyl)-1,3,5-triazin-2-yl)-5-propoxyphenol, 2-(4-amino-6-(2,4-dibutoxyphenyl)-1,3,5-triazin-2-yl)-5-butoxyphenol, 2-(4-amino-6-(2,4-dibutoxyphenyl)-1,3,5-triazin-2-yl)-5-butoxyphenol, 2-(4-amino-6-(2,4-dipentoxyphenyl)-1,3,5-triazin-2-yl)-5-pentoxyphenol, 2-(4-amino-6-(2,4-dipentoxyphenyl)-1,3,5-triazin-2-yl)-5-pentoxyphenol, 2-(4-amino-6-(2,4-dihexoxyphenyl)-1,3,5-triazin-2-yl)-5-hexoxyphenol, 2-(4-amino-6-(2,4-dihexoxyphenyl)-1,3,5-triazin-2-yl)-5-hexoxyphenol, 2-(4-amino-6-(2,4-diheptoxyphenyl)-1,3,5-triazin-2-yl)-5-heptoxyphenol, 2-(4-amino-6-(2,4-diheptoxyphenyl)-1,3,5-triazin-2-yl)-5-heptoxyphenol, 4,6-di([1,1'-biphenyl]-4-yl)-1,3,5-triazin-2-amine, 2,2'-(((6-amino-1,3,5-triazine-2,4-diyl)bis(3-hydroxy-4,1-phenylene))bis(oxy))dipropionic acid, dimethyl 2,2'-(((6-amino-1,3,5-triazine-2,4-diyl)bis(3-hydroxy-4,1-phenylene))bis(oxy))dipropionate, dinonyl 2,2'-(((6-amino-1,3,5-triazine-2,4-diyl)bis(3-hydroxy-4,1-phenylene))bis(oxy))dipropionate, dioctyl 2,2'-(((6-amino-1,3,5-triazine-2,4-diyl)bis(3-hydroxy-4,1-phenylene))bis(oxy))dipropionate, didecyl 2,2'-(((6-amino-1,3,5-triazine-2,4-diyl)bis(3-hydroxy-4,1-phenylene))bis(oxy))dipropionate, didodecyl 2,2'-(((6-amino-1,3,5-triazine-2,4-diyl)bis(3-hydroxy-4,1-phenylene))bis(oxy))dipropionate, diisooctyl 2,2'-(((6-amino-1,3,5-triazine-2,4-diyl)bis(3-hydroxy-4,1-phenylene))bis(oxy))dipropionate, diheptyl 2,2'-(((6-amino-1,3,5-triazine-2,4-diyl)bis(3-hydroxy-4,1-phenylene))bis(oxy))dipropionate, dihexyl 2,2'-(((6-amino-1,3,5-triazine-2,4-diyl)bis(3-hydroxy-4,1-phenylene))bis(oxy))dipropionate, dipentyl 2,2'-(((6-amino-1,3,5-triazine-2,4-diyl)bis(3-hydroxy-4,1-phenylene))bis(oxy))dipropionate, 4,4'-(6-amino-1,3,5-triazine-2,4-diyl)bis(benzene-1,3-diol), 4,6-bis(2,4-dimethylphenyl)-1,3,5-triazin-2-amine, and 4,6-diphenyl-1,3,5-triazin-2-amine.

In another preferred embodiment, the at least one diazotizing reagent is selected from the group consisting of at least one alkyl nitrite and at least one compound of formula $G(NO_2)_o$ in combination with at least one acid;
wherein G is selected from the group consisting of Na, K, Li, Mg, Cs and Ba; and
is 1 to 2;
more preferably G is Na and K; and o is 1.

In another preferred embodiment, the $G(NO_2)_o$ is selected from the group consisting of $NaNO_2$, $KNO_2$, $Mg(NO_2)_2$, $LiNO_2$, $Ba(NO_2)_2$ and $Ca(NO_2)_2$; most preferably $NaNO_2$ and $KNO_2$.

In another preferred embodiment, at least one acid used in the process of diazotization is selected from the group consisting of inorganic acids and organic acids.

In another preferred embodiment, the at least one inorganic acid used in the process of diazotization is selected from the group consisting of sulfuric acid, hydrochloric acid, phosphoric acid ($H_3PO_4$), phosphorous acid ($H_3PO_3$), phosphinic acid ($H_3PO_2$), perchloric acid, nitric acid, nitrous acid, sulphurous acid, chloric acid, chlorous acid and hypochlorous acid; more preferably the at least one inorganic acid used in the process of diazotization is hydrochloric acid.

In another preferred embodiment, the at least one organic acid used in the process of diazotization is selected from the group consisting organic carboxylic acid and organic sulfonic acid.

In another preferred embodiment, the at least one organic carboxylic acid used in the process of diazotization is selected from the group consisting of acetic acid, formic acid, propionic acid, butanoic acid, benzoic acid, phthalic acid, oxalic acid, malonic acid, succinic acid, glutaric acid, adipic acid, lactic acid, citric acid, uric acid and malic acid; more preferably the at least one organic carboxylic acid used in the process of diazotization is selected from the group consisting of acetic acid, formic acid, propionic acid, butanoic acid and benzoic acid; most preferably the at least one organic carboxylic acid used in the process of diazotization is selected from the group consisting of acetic acid and formic acid.

In a preferred embodiment, the organic sulfonic acid used in the process of diazotization is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid, more preferably the organic sulfonic acid used in the process of diazotization is selected from the group consisting of methanesulfonic acid, trifluoromethanesulfonic acid, benzenesulfonic acid and p-toluenesulfonic acid, even more preferably the organic sulfonic acid used in the process of diazotization is selected from the group consisting of methanesulfonic acid and p-toluenesulfonic acid.

In another preferred embodiment, the at least one alkyl nitrite is selected from the group consisting of tert-butyl nitrite and isoamyl nitrite, more preferably the at least one alkyl nitrite is isoamyl nitrile.

In another preferred embodiment, the at least one diazotizing reagent comprising alkyl nitrite further comprises at least one chlorotrialkylsilane.

In another preferred embodiment, the at least one chlorotrialkylsilane is selected from the group consisting of chlorotrimethyl silane, chlorotriethyl silane, chlorodimethylethyl silane, chlorodiethylmethyl silane, tert-butyl chlorodimethylsilane, more preferably the at least one chlorotrialkylsilane is selected from the group consisting of chlorotrimethyl silane chlorotriethylsilane and tert-butyl chlorodimethylsilane.

In another preferred embodiment, the process of diazotization is carried out in the presence of at least one solvent selected from the group consisting of aliphatic and aromatic hydrocarbons, halogenated aliphatic, halogenated aromatic hydrocarbons, ethers and carbon disulphide, more preferably aliphatic and aromatic hydrocarbons, halogenated aliphatic, halogenated aromatic hydrocarbons, most preferably aromatic hydrocarbons, halogenated aliphatic and halogenated aromatic hydrocarbons, and more preferably in aromatic hydrocarbons and halogenated aromatic hydrocarbons.

In another preferred embodiment, the step i) is carried out at a temperature in the range of 0 to 220° C., more preferably the step i) is carried out at a temperature in the range of 50 to 200° C., even more preferably, the step i) is carried out at a temperature in the range of 80 to 180° C., most preferably the step i) is carried out at a temperature in the range of 100 to 180° C. and in particular preferably the step i) is carried out at a temperature in the range of 120 to 180° C.

In another preferred embodiment, the step i) is carried out in the presence of at least one solvent selected from the group consisting of aliphatic and aromatic hydrocarbons, halogenated aliphatic, halogenated aromatic hydrocarbons, ethers and carbon disulphide, more preferably the step i) is carried out in the presence of at least one solvent selected from the group consisting of aliphatic and aromatic hydrocarbons, halogenated aliphatic, halogenated aromatic hydrocarbons, most preferably the step i) is carried out in the presence of at least one solvent selected from the group consisting of aromatic hydrocarbons, halogenated aliphatic and halogenated aromatic hydrocarbons, and in preferably the step i) is carried out in the presence of at least one solvent selected from the group consisting of aromatic hydrocarbons and halogenated aromatic hydrocarbons.

In another preferred embodiment, the weight ratio of the diazotizing agent to the at least one compound of formula (A) is in the range of 2:1 to 10:1', more preferably 2:1 to 6:1, most preferably 2:1 to 5:1 and in particular preferably 2:1 to 3:1.

In another preferred embodiment, the step i) is carried out for a period of 30 minutes to 24 hours, more preferably 30 minutes to 15 hours, even more preferably 1 hour to 10 hours, most preferably 1 hour to 6 hours, and in particular preferably 1 hour to 5 hours.

In another preferred embodiment, the at least one reagent of formula $M(M_a)_n$ is selected from the group consisting of CuT, HT, Kl and $BF_4^-$, wherein T is selected from CN, F, Cl and Br.

In another preferred embodiment, the at least one reagent of formula $M(M_a)_n$ is selected from the group consisting CuCN, CuCl, CuBr, CuI, HCN, HCl, HBr, Hl, Kl and $BF_4^-$, more preferably CuCl, CuBr, CuI, HCl, HBr, Hl, Kl and $BF_4^-$, most preferably CuCl, CuBr, HCl and HBr.

In another preferred embodiment, the step ii) is carried out at a temperature in the range of 0 to 200° C., more preferably the temperature in the range of 0 to 150° C., most preferably the temperature in the range of 0 to 100° C. and in particular preferably the temperature in the range of 0 to 100° C.

In another preferred embodiment, the weight ratio of the at least one reagent of formula $M(M_a)_n$ to the at least one compound of formula (Aa) is in the range of 1:2 to 20:2, more preferably in the range of 1:2 to 15:2, most preferably in the range of 1:2 to 5:1, and in particular preferably in the range of 1:2 to 3:1.

In another preferred embodiment, the step ii) is carried out for a period of 30 minutes to 24 hours, more preferably 30 minutes to 15 hours, even more preferably 1 hour to 10 hours, most preferably 1 hour to 6 hours, and in particular preferably 1 hour to 5 hours.

The compound of formula (D) formed in the reaction is isolated by any method known in the art selected from the group consisting of chemical separation, acid-base neutralization, distillation, evaporation, column chromatography, filtration, concentration, crystallization and re-crystallization or a combination thereof. A person skilled in the art is aware of such techniques.

In an embodiment the presently claimed invention is directed to a process for preparing a compound of formula (F),

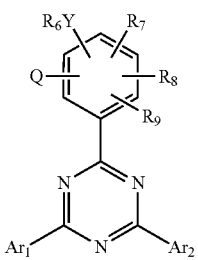

formula (F)

wherein $Ar_1$ and $Ar_2$ are the same or different and are as defined as above,
Q is selected from hydrogen and OH;
$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_s$—$C_{24}$ cycloalkenyl, and C(=O)R;
$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal,
R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, optionally with either of $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, Re or $R_9$ is NRR', R and R' are not both hydrogen, and
Y is independently selected from the group consisting of hydrogen, halogen, O, —NR", or S, wherein R" is hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl; when Y is a hydrogen or halogen then $R_6$ is absent,
comprising at least the steps of reacting at least one compound of formula (D),

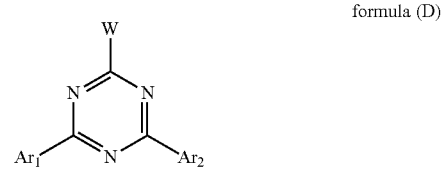

formula (D)

wherein W is halogen,
$Ar_1$ and $Ar_2$ are the same or different and are as defined as above
and at least one compound of formula (E),

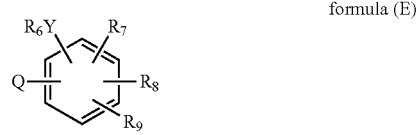

formula (E)

wherein
Q is selected from hydrogen and OH;
$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$alkenyl, substituted or unsubstituted $C_6$-$C_{24}$aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, optionally with either of $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is independently selected from the group consisting of hydrogen, halogen, O, —NR", or S, wherein R" is hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl; when Y is a hydrogen or halogen then $R_6$ is absent.

In the presence of at least one acid.

In a preferred embodiment, $R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, and C(=O)R; more preferably, $R_6$ is selected from the group consisting of hydrogen, substituted or unsubstituted linear or branched $C_1$-$C_{24}$ alkyl, substituted or unsubstituted $C_6$-$C_{24}$ aryl, substituted or unsubstituted $C_7$-$C_{24}$ arylalkyl, and C(=O)R. Most preferably, $R_6$ is selected from the group consisting of hydrogen, substituted or unsubstituted linear or branched $C_1$-$C_{24}$ alkyl, substituted and C(=O)R; and in particular preferably, $R_6$ is selected from the group consisting of hydrogen, substituted or unsubstituted linear or branched $C_1$-$C_{24}$ alkyl and substituted.

In another preferred embodiment, $R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, optionally with either of $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen;

more preferably $R_7$, $R_8$ and $R_9$ are independently selected from the group consisting of hydrogen, halogen, substituted or unsubstituted linear or branched $C_1$-$C_{24}$ alkyl, substituted or unsubstituted $C_6$-$C_{24}$ aryl, substituted or unsubstituted $C_7$-$C_{24}$ arylalkyl, C(=O)R, OR, NRR', C(=O)NRR', OCOR and CN; R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, optionally with either of R, and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen;

even more preferably $R_7$, $R_8$ and $R_9$ are independently selected from the group consisting of hydrogen, halogen, substituted or unsubstituted linear or branched $C_1$-$C_{24}$ alkyl, substituted or unsubstituted $C_2$-$C_{24}$ aryl, substituted or unsubstituted $C_7$-$C_{24}$ arylalkyl, C(=O)R, OR, NRR', C(=O)NRR', OCOR, CN, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl; most preferably $R_7$, $R_8$ and $R_9$ are independently selected from the group consisting of hydrogen, halogen, substituted or unsubstituted linear or branched $C_1$-$C_{24}$ alkyl, substituted or unsubstituted $C_6$-$C_{24}$ aryl, substituted or unsubstituted $C_7$-$C_{24}$ arylalkyl, OR, OCOR, R is selected from the group consisting of hydrogen and substituted or unsubstituted linear or branched $C_1$-$C_{24}$ alkyl;

and in particular preferably $R_7$, $R_8$ and $R_9$ are independently selected from the group consisting of hydrogen, halogen, substituted or unsubstituted linear or branched $C_1$-$C_{24}$ alkyl, OR, OCOR, R is selected from the group consisting of hydrogen and substituted or unsubstituted linear or branched $C_1$-$C_{24}$ alkyl.

In another preferred embodiment, Y is selected from the group consisting of hydrogen, halogen, O, —NR", or S, wherein R" is hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl; when Y is a hydrogen or halogen then $R_6$ is absent;

more preferably, Y is selected from the group consisting of hydrogen, halogen, O; when Y is a hydrogen or halogen then $R_6$ is absent;

most preferably, Y is selected from the group consisting of hydrogen and O; when Y is a hydrogen then $R_6$ is absent.

In another preferred embodiment, the terms substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl are same as defined above.

In a preferred embodiment, the compound of formula (D) is selected from the group consisting of 2-(4-chloro-6-(2,4-dipropoxyphenyl)-1,3,5-triazin-2-yl)-5-propoxyphenol, 2-(4-bromo-6-(2,4-dipropoxyphenyl)-1,3,5-triazin-2-yl)-5-propoxyphenol, 2-(4-iodo-6-(2,4-dipropoxyphenyl)-1,3,5-triazin-2-yl)-5-propoxyphenol, 4-(2,4-dipropoxyphenyl)-6-(2-hydroxy-4-propoxyphenyl)-1,3,5-triazin-2-yl methanesulfonate, 4-(2,4-dipropoxyphenyl)-6-(2-hydroxy-4-propoxyphenyl)-1,3,5-triazin-2-yl trifluoromethanesulfonate, 2-(4-chloro-6-(2,4-dibutoxyphenyl)-1,3,5-triazin-2-yl)-5-butoxyphenol, 2-(4-bromo-6-(2,4-dibutoxyphenyl)-1,3,5-triazin-2-yl)-5-butoxyphenol, 2-(4-chloro-6-(2,4-dipentoxyphenyl)-1,3,5-triazin-2-yl)-5-pentoxyphenol, 2-(4-bromo-6-(2,4-dipentoxyphenyl)-1,3,5-triazin-2-yl)-5-pentoxyphenol, 2-(4-chloro-6-(2,4-dihexoxyphenyl)-1,3,5-triazin-2-yl)-5-hexoxyphenol, 2-(4-bromo-6-(2,4-dihexoxyphenyl)-1,3,5-triazin-2-yl)-5-hexoxyphenol, 2-(4-chloro-6-(2,4-diheptoxyphenyl)-1,3,5-triazin-2-yl)-5-heptoxyphenol, 2-(4-bromo-6-(2,4-diheptoxyphenyl)-1,3,5-triazin-2-yl)-5-heptoxyphenol, 2,4-di([1,1'-biphenyl]-4-yl)-6-chloro-1,3,5-triazine, 2,2'-(((6-chloro-1,3,5-triazine-2,4-diyl)bis(3-hydroxy-4,1-phenylene))bis(oxy))dipropionic acid, dimethyl 2,2'-(((6-bromo-1,3,5-triazine-2,4-diyl)bis(3-hydroxy-4,1-phenylene))bis(oxy))dipropionate, dinonyl 2,2'-(((6-chloro-1,3,5-triazine-2,4-diyl)bis(3-hydroxy-4,1-phenylene))bis(oxy))dipropionate, dioctyl 2,2'-(((6-bromo-1,3,5-triazine-2,4-diyl)bis(3-hydroxy-4,1-phenylene))bis(oxy))dipropionate, didecyl 2,2'-(((6-chloro-1,3,5-triazine-2,4-diyl)bis(3-hydroxy-4,1-phenylene))bis(oxy))dipropionate, didodecyl 2,2'-(((6-bromo-1,3,5-triazine-2,4-diyl)bis(3-hydroxy-4,1-phenylene))bis(oxy))dipropionate, diisooctyl 2,2'-(((6-chloro-1,3,5-triazine-2,4-diyl)bis(3-hydroxy-4,1-phenylene))bis(oxy))dipropionate, diheptyl 2,2'-(((6-bromo-1,3,5-triazine-2,4-diyl)bis(3-hydroxy-4,1-phenylene))bis(oxy))dipropionate, dihexyl 2,2'-(((6-chloro-1,3,5-triazine-2,4-diyl)bis(3-hydroxy-4,1-phenylene))bis(oxy))dipropionate, dipentyl 2,2'-(((6-bromo-1,3,5-triazine-2,4-diyl)bis(3-hydroxy-4,1-phenylene))bis(oxy))dipropionate, 4,4'-(6-chloro-1,3,5-triazine-2,4-diyl)bis(benzene-1,3-diol), 2-chloro-4,6-bis(2,4-dimethylphenyl)-1,3,5-triazine, and 2-bromo-4,6-diphenyl-1,3,5-triazine.

In a preferred embodiment, the compound of formula (E) is selected from the group consisting of phenol, o-cresol, m-cresol, hydroquinone, 2,5-dimethylphenol, 2,4-dimethylphenol, 2,3-dimethylphenol, 2,3,5-trimethylphenol, 2,3,4-trimethylphenol, 3,4,5-trimethylphenol, 1-methoxy-2,3,5-trimethylbenzene, 1-methoxy-2-methylbenzene, 1-methoxy-3-methylbenzene, 1-methoxy-4-methylbenzene, 1-methoxy-2,3-dimethylbenzene, 1-methoxy-2,4-dimethylbenzene, 1-methoxy-2,5-dimethylbenzene, 1-methoxy-2,6-dimethylbenzene, 1-methoxy-3,4-dimethylbenzene, 1-methoxy-3,5-dimethylbenzene, 1-methoxy-3,6-dimethylbenzene, 1-(ethoxy)-2-methylbenzene, 1-(propoxy)-2-methylbenzene, 1-(butoxy)-2-methylbenzene, 1-(pentoxy)-2-methylbenzene, 1-(hexyloxy)-2-methylbenzene, 1-(heptyloxy)-2-methylbenzene, 1-(octyloxy)-2-methylbenzene, 1-(nonyloxy)-2-methylbenzene, 1-(decyloxy)-2-methylbenzene, 1-(undecyloxy)-2-methylbenzene, 1-(dodecyloxy)-2-methylbenzene, 1-(tridecyloxy)-2-methylbenzene, 1-(tetradecyloxy)-2-methylbenzene, 1-(pentadecyloxy)-2-methylbenzene, 1-(hexadecyloxy)-2-methylbenzene, 1-(heptadecyloxy)-2-methylbenzene, 1-(octadecyloxy)-2-methylbenzene, 1-(nonadecyloxy)-2-methylbenzene, 1-(icosyloxy)-2-methylbenzene, 1-(henicosyloxy)-2-methylbenzene, 1-(docosyloxy)-2-methylbenzene, 1-(methoxy)-3-methylbenzene, 1-(ethoxy)-3-methylbenzene, 1-(propoxy)-3-methylbenzene, 1-(butoxy)-3-methylbenzene, 1-(pentoxy)-3-methylbenzene, 1-(hexyloxy)-3-methylbenzene, 1-(heptyloxy)-3-methylbenzene, 1-(octyloxy)-3-methylbenzene, 1-(nonyloxy)-3-methylbenzene, 1-(decyloxy)-3-methylbenzene, 1-(undecyloxy)-3-methylbenzene, 1-(dodecyloxy)-3-methylbenzene, 1-(tridecyloxy)-3-methylbenzene, 1-(tetradecyloxy)-3-methylbenzene, 1-(pentadecyloxy)-3-methylbenzene, 1-(hexadecyloxy)-3-methylbenzene, 1-(heptadecyloxy)-3-methylbenzene, 1-(octadecyloxy)-3-methylbenzene, 1-(nonadecyloxy)-3-methylbenzene, 1-(icosyloxy)-3-methylbenzene, 1-(henicosyloxy)-3-methylbenzene, 1-(docosyloxy)-3-methylbenzene, 1-(methoxy)-4-methylbenzene, 1-(ethoxy)-4-methylbenzene, 1-(propoxy)-4-methylbenzene, 1-(butoxy)-4-methylbenzene, 1-(pentoxy)-4-methylbenzene, 1-(hexyloxy)-4-methylbenzene, 1-(heptyloxy)-4-methylbenzene, 1-(octyloxy)-4-methylbenzene, 1-(nonyloxy)-4-methylbenzene, 1-(decyloxy)-4-methylbenzene, 1-(undecyloxy)-4-methylbenzene, 1-(dodecyloxy)-4-methylbenzene, 1-(tridecyloxy)-4-methylbenzene, 1-(tetradecyloxy)-4-methylbenzene, 1-(pentadecyloxy)-4-methylbenzene, 1-(hexadecyloxy)-4-methylbenzene, 1-(heptadecyloxy)-4-methylbenzene, 1-(octadecyloxy)-4-methylbenzene, 1-(nonadecyloxy)-4-methylbenzene, 1-(icosyloxy)-4-methylbenzene, 1-(henicosyloxy)-4-methylbenzene, 1-(docosyloxy)-4-methylbenzene, 1-methyl-2-(vinyloxy)benzene, 1-methyl-2-(prop-1-en-1-yloxy)benzene, 1-(but-1-en-1-yloxy)-2-methylbenzene, 1-methyl-2-(pent-1-en-1-yloxy)benzene, 1-(hex-1-en-1-yloxy)-2-methylbenzene, 1-(hept-1-en-1-yloxy)-2-methylbenzene, 1-(oct-1-en-1-yloxy)-2-methylbenzene, 1-(non-1-en-1-yloxy)-2-methylbenzene, 1-(dec-1-en-1-yloxy)-2-methylbenzene, 1-(undec-1-en-1-yloxy)-2-methylbenzene, 1-(dodec-1-en-1-yloxy)-2-methylbenzene, 1-(tridec-1-en-1-yloxy)-2-methylbenzene, 1-(tetradec-1-en-1-yloxy)-2-methylbenzene, 1-(pentadec-1-en-1-yloxy)-2-methylbenzene, 1-(hexadec-1-en-1-yloxy)-2-methylbenzene, 1-(heptadec-1-en-1-yloxy)-2-methylbenzene, 1-(octadec-1-en-1-yloxy)-2-methylbenzene, 1-(nonadec-1-en-1-yloxy)-2-methylbenzene, 1-(icos-1-en-1-yloxy)-2-methylbenzene, 1-(henicos-1-en-1-yloxy)-2-methylbenzene, 1-(docos-1-en-1-yloxy)-2-methylbenzene, 3-methoxy-2-methylphenol, 3-ethoxy-2-methylphenol, 3-propoxy-2-methylphenol, 3-butoxy-2-methylphenol, 3-pentyloxy-2-methylphenol, 3-hexyloxy-2-methylphenol, 3-heptyloxy-2-methylphenol, 3-octylxy-2-methylphenol, 3-nonylxy-2-methylphenol, 3-(decyloxy)-2-methylphenol, 3-(undecyloxy)-2-methylphenol, 3-(dodecyloxy)-2-methylphenol, 3-(tridecyloxy)-2-methylphenol, 3-(tetradecyloxy)-2-methylphenol, 3-(pentadecyloxy)-2-methylphenol, 3-(hexadecyloxy)-2-methylphenol, 3-(heptadecyloxy)-2-methylphenol, 3-(octadecyloxy)-2-methylphenol, 3-(nonadecyloxy)-2-methylphenol, 3-(icosyloxy)-2-methylphenol, 3-(henicosyloxy)-2-methylphenol, 3-(docosyloxy)-2-methylphenol, 3-(3-hydroxyphenoxy)propane-1,2-diol, 3-(2-hydroxy-3-methoxypropoxy)phenol, 3-(3-ethoxy-2-hydroxypropoxy)phenol, 3-(2-hydroxy-3-propoxypropoxy)phenol, 3-(3-butoxy-2-hydroxypropoxy)phenol, 3-(2-hydroxy-3-(pentyloxy)propoxy)phenol, 3-(3-(hexan-2-yloxy)-2-hydroxypropoxy)phenol, 3-(2-hydroxy-3-(pentan-2-yloxy)propoxy)phenol, 3-(3-(sec-butoxy)-2-hydroxypropoxy)phenol, 3-(2-hydroxy-3-isopropoxypropoxy)phenol, 3-(2-hydroxy-3-(undecyloxy)propoxy)phenol, 3-(2-hydroxy-3-(dodecyloxy)propoxy)phenol, 3-(2-hydroxy-3-(tridecyloxy)propoxy)phenol, 3-(2-hydroxy-3-(tetradecyloxy)propoxy)phenol, 3-(2-hydroxy-3-(pentadecyloxy)propoxy)phenol, 3-(2-hydroxy-3-(hexadecyloxy)propoxy)phenol, 3-(2-hydroxy-3-(heptadecyloxy)propoxy)phenol, 3-(2-hydroxy-3-(octadecyloxy)propoxy)phenol, 3-(2-hydroxy-3-(nonadecyloxy)propoxy)phenol, 3-(2-hydroxy-3-(nonan-5-yloxy)propoxy)phenol, 3-methoxyphenol, 3-ethoxyphenol, 3-butoxyphenol, 3-(pentyloxy)phenol, 3-(hexyloxy)phenol, 3-(heptyloxy)phenol, 3-(octyloxy)phenol, 3-(nonyloxy)phenol, 3-(decyloxy)phenol, 3-(undecyloxy)phenol, 3-(dodecyloxy)phenol, 3-(tridecyloxy)phenol, 3-(tetradecyloxy)phenol, 3-(pentadecyloxy)phenol, 3-(hexadecyloxy)phenol, 3-(heptadecyloxy)phenol, 3-(octadecyloxy)phenol, 3-(nonadecyloxy)phenol, 3-(icosyloxy)phenol, 3-(henicosyloxy)phenol, 3-(docosyloxy)phenol, 2-methoxyphenol, 2-ethoxyphenol, 2-butoxyphenol, 2-(pentyloxy)phenol, 2-(hexyloxy)phenol, 2-(heptyloxy)phenol, 2-(octyloxy)phenol, 2-(nonyloxy)phenol, 2-(decyloxy)phenol, 2-(undecyloxy)phenol, 2-(dodecyloxy)phenol, 2-(tridecyloxy)phenol, 2-(tetradecyloxy)phenol, 2-(pentadecyloxy)phenol, 2-(hexadecyloxy)phenol, 2-(heptadecyloxy)phenol, 2-(octadecyloxy)phenol, 2-(nonadecyloxy)phenol, 2-(icosyloxy)phenol, 2-(henicosyloxy)phenol, 2-(docosyloxy)phenol, 4-methoxyphenol, 4-ethoxyphenol, 4-butoxyphenol, 4-(pentyloxy)phenol, 4-(hexyloxy)phenol, 4-(heptyloxy)phenol, 4-(octyloxy)phenol, 4-(nonyloxy)phenol, 4-(decyloxy)phenol, 4-(undecyloxy)phenol, 4-(dodecyloxy)phenol, 4-(tridecyloxy)phenol, 4-(tetradecyloxy)phenol, 4-(pentadecyloxy)phenol, 4-(hexadecyloxy)phenol, 4-(heptadecyloxy)phenol, 4-(octadecyloxy)phenol, 4-(nonadecyloxy)phenol, 4-(icosyloxy)phenol, 4-(henicosyloxy)phenol, 4-(docosyloxy)phenol, 3-(2-hydroxy-3-(2-methylbutoxy)propoxy)phenol, 3-(3-(2-ethylbutoxy)-2-hydroxypropoxy)phenol, 3-(3-((2-ethylpentyl)oxy)-2-hydroxypropoxy)phenol, 3-(3-((2-ethylhexyl)oxy)-2-hydroxypropoxy)phenol, 3-(3-((2-ethylheptyl)oxy)-2-hydroxypropoxy)phenol, 3-(3-((2-ethyloctyl)oxy)-2-hydroxypropoxy)phenol, 3-(3-((2-ethylnonyl)oxy)-2-hydroxypropoxy)phenol, 3-(3-((2-ethyldecyl)oxy)-2-hydroxypropoxy)phenol, 3-(3-((2-ethylundecyl)oxy)-2-hydroxypropoxy)phenol, 3-(3-((2-ethyldodecyl)oxy)-2-hydroxypropoxy)phenol, 3-(3-((2-ethyltridecyl)oxy)-2-hydroxypropoxy)phenol, 3-(3-((2-ethyltetradecyl)oxy)-2-hydroxypropoxy)phenol, 3-(3-((2-ethylpentadecyl)oxy)-2-hydroxypropoxy)phenol, 3-(3-((2-ethylhexadecyl)oxy)-2-hydroxypropoxy)phenol, 3-(3-((2-ethylheptadecyl)oxy)-2-hydroxypropoxy)phenol, 3-(3-((2-ethyloctadecyl)oxy)-2-hydroxypropoxy)phenol, 3-(3-((2-ethylnonadecyl)oxy)-2-hydroxypropoxy)phenol, 3-(3-((2-ethylicosyl)oxy)-2-hydroxypropoxy)phenol, 2-(3-hydroxyphenoxy)propanoic acid, methyl 2-(3-hydroxyphenoxy)propanoate, ethyl 2-(3-hydroxyphenoxy)propanoate, propyl 2-(3-hydroxyphenoxy)propanoate, butyl 2-(3-hydroxyphenoxy)propanoate, pentyl 2-(3-hydroxyphenoxy)propanoate, hexyl 2-(3-hydroxyphenoxy)propanoate, heptyl 2-(3-hydroxyphenoxy)propanoate, octyl 2-(3-hydroxyphenoxy)propanoate, nonyl 2-(3-hydroxyphenoxy)propanoate, decyl 2-(3-hydroxyphenoxy)propanoate, undecyl 2-(3-hydroxyphenoxy)propanoate, dodecyl 2-(3-hydroxyphenoxy)propanoate, tridecyl 2-(3-hydroxyphenoxy)propanoate, tetradecyl 2-(3-hydroxyphenoxy)propanoate, pentadecyl 2-(3-hydroxyphenoxy)propanoate, hexadecyl 2-(3-hydroxyphenoxy)propanoate, heptadecyl 2-(3-hydroxyphenoxy)propanoate, octadecyl 2-(3-hydroxyphenoxy)propanoate, nonadecyl 2-(3-hydroxyphenoxy)propanoate, icosyl 2-(3-hydroxyphenoxy)propanoate, 1,1'-biphenyl, [1,1'-biphenyl]-4-ol, [1,1'-biphenyl]-3-ol, [1,1'-biphenyl]-2-ol, 2-methyl-[1,1'-biphenyl]-3-ol, 6-methyl-[1,1'-biphenyl]-3-ol, 5-methyl-[1,1'-biphenyl]-3-ol, 3-methyl-1,1'-biphenyl.

In another preferred embodiment, the at least one acid used in the process for preparing a compound of formula (F) is selected from the group consisting of inorganic acid, Lewis acid, and organic acid.

In another preferred embodiment, the at least one inorganic acid used in the process for preparing a compound of formula (F) is selected from the group consisting of sulfuric acid, hydrochloric acid, phosphoric acid ($H_3PO_4$), phosphorous acid ($H_3PO_3$), phosphinic acid ($H_3PO_2$), perchloric acid, nitric acid, nitrous acid, sulphurous acid, chloric acid, chlorous acid and hypochlorous acid; more preferably the at least one inorganic acid used in the process for preparing a compound of formula (F) is hydrochloric acid.

In another preferred embodiment, the at least one Lewis acid used in the process for preparing a compound of formula (F) is selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or 1; $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, $Li(acetate)$, $Zr(acetylacetonate)_4$, $Si(acetate)_4$, $K(acetate)$, $Na(acetate)$, $Cs(acetate)$, $Rb(acetate)$, $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, $Ag(acetate)$, $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri-fluoromethanesulfonate)_2$ and $Cu(tosylate)_2$; more preferably the Lewis acid is selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NIX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; most preferably selected from the group consisting of $BX_3$, $BX_3$—$(C_2H_5)_2O$, $BX_3$—$S(CH_3)_2$, $AlX_3$, $(C_2H_5)_2AlX$, $TiX_2$, $TiX_4$ whereby X in each case denotes F, Cl, Br, $S(=O)_3$, $CF_3$—$S(=O)_2O$, $CH_3$—$S(=O)_2O$, or I; In particular preferably selected from the group consisting of $BX_3$, $AlX_3$, $(C_2H_5)_2AlX$, whereby X in each case denotes F, Cl, Br, $CF_3$—$S(=O)_2O$, $CH_3$—$S(=O)_2O$, or I.

In another preferred embodiment, the at least one Lewis acid used in the process for preparing a compound of formula (F) is selected from the group consisting of $BX_3$, $BX_3$—$(C_2H_5)_2O$, $BX_3$—$S(CH_3)_2$, $AlX_3$, $ZnX_2$, $FeX_3$ and $TiX_4$, whereby X in each case denotes F, Cl, or Br.

In another preferred embodiment, the at least one organic acid used in the process for preparing a compound of formula (F) is selected from the group consisting organic carboxylic acid and organic sulfonic acid.

In another preferred embodiment, the at least one organic carboxylic acid used in the process for preparing a compound of formula (F) is selected from the group consisting of acetic acid, formic acid, propionic acid, butanoic acid, benzoic acid, phthalic acid, oxalic acid, malonic acid, succinic acid, glutaric acid, adipic acid, lactic acid, citric acid, uric acid and malic acid; more preferably the at least one organic carboxylic acid used in the process for preparing a compound of formula (F) is selected from the group consisting of acetic acid, formic acid, propionic acid, butanoic acid and benzoic acid; most preferably the at least one organic carboxylic acid used in the process for preparing a compound of formula (F) is selected from the group consisting of acetic acid and formic acid.

In a preferred embodiment, the organic sulfonic acid used in the process for preparing a compound of formula (F) is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid, more preferably the organic sulfonic acid used in the process for preparing a compound of formula (F) is selected from the group consisting of methanesulfonic acid, trifluoromethanesulfonic acid, benzenesulfonic acid and p-toluenesulfonic acid, even more preferably the organic sulfonic acid used in the process for preparing a compound of formula (F) is selected from the group consisting of methanesulfonic acid and p-toluenesulfonic acid.

In another preferred embodiment, the at least one Lewis acid catalyst used in the process for preparing a compound of formula (F) is selected from the group consisting of $BX_3$, $BX_3$—$(C_2H_5)_2O$, $BX_3$—$S(CH_3)_2$, $AlX_3$, $ZnX_2$ and $TiX_4$, whereby X in each case denotes F, Cl, or Br.

In another preferred embodiment, the molar ratio of the at least one Lewis acid to the at least one compound of formula (D) is in in the range of 1:10 to 10:1; more preferably in in the range of 1:8 to 8:1; even more in in the range of 1:5 to 5:1; most preferably in in the range of 1:3 to 3:1; and in particular preferably in in the range of 1:2 to 2:1.

In another preferred embodiment, the molar ratio of the at least one acid, preferably the at least Lewis acid, to the at least one compound of formula (E) is in in the range of 1:10 to 10:1; more preferably in in the range of 1:8 to 8:1; even more in in the range of 1:5 to 5:1; most preferably in in the range of 1:3 to 3:1; and in particular preferably in in the range of 1:2 to 2:1.

In another preferred embodiment, the molar ration of the at least one compound of formula (D) to the at least one compound of formula (E) is in the range of 2:5 to 5:2; more preferably in the range of 1:2 to 2:1; and most preferably in the range of 1:1 to 2:1.

In another preferred embodiment, the at least one compound of formula (D) and the at least one compound of formula (E) is carried out in the presence of at least one solvent selected from the group consisting of aliphatic and aromatic hydrocarbons, halogenated aliphatic, halogenated aromatic hydrocarbons, ethers and carbon disulphide, more preferably aliphatic and aromatic hydrocarbons, halogenated aliphatic, halogenated aromatic hydrocarbons, most preferably aromatic hydrocarbons, halogenated aliphatic and halogenated aromatic hydrocarbons, and even more preferably in aromatic hydrocarbons and halogenated aromatic hydrocarbons.

In another preferred embodiment, the at least one compound of formula (E) and the at least one compound of formula (D) are reacted at a temperature in the range of 0 to 250° C., more preferably at a temperature in the range of 50 to 200° C., even more preferably, at a temperature in the range of 80 to 180° C., most preferably at a temperature in the range of 100 to 180° C. and in particular preferably at a temperature in the range of 120 to 180° C.

In another preferred embodiment, the at least one compound of formula (E) and the at least one compound of formula (D) are reacted for a period of 30 minutes to 24 hours, more preferably 30 minutes to 15 hours, even more preferably 1 hour to 10 hours, most preferably 1 hour to 6 hours, and in particular preferably 1 hour to 5 hours.

The compound of formula (F) formed in the reaction is isolated by any method known in the art selected from the group consisting of chemical separation, acid-base neutralization, distillation, evaporation, column chromatography, filtration, concentration, crystallization and re-crystallization or a combination thereof. A person skilled in the art is aware of such techniques.

The representative UV absorber compounds have been synthesized using presently claimed process are

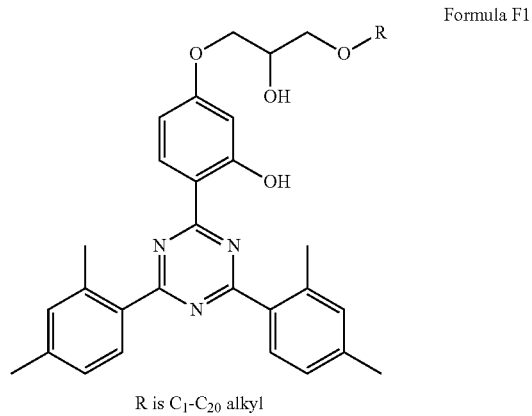

Formula F1

R is $C_1$-$C_{20}$ alkyl

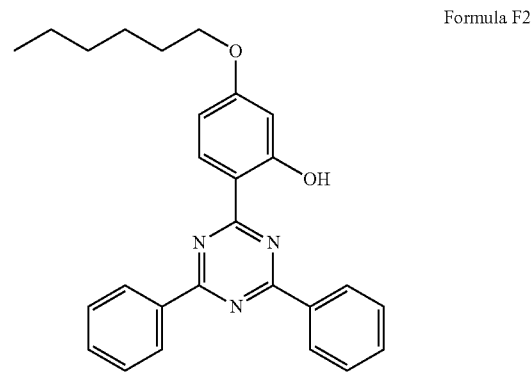

Formula F2

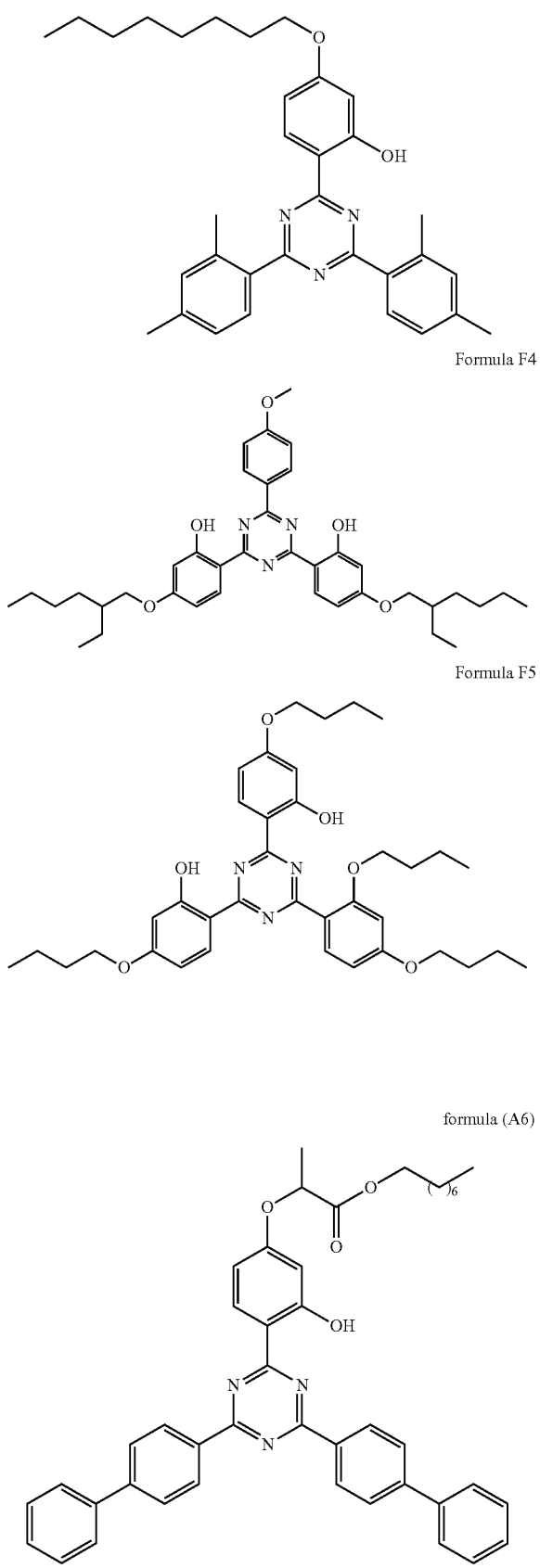

Formula F3

Formula F4

Formula F5 formula (A6)

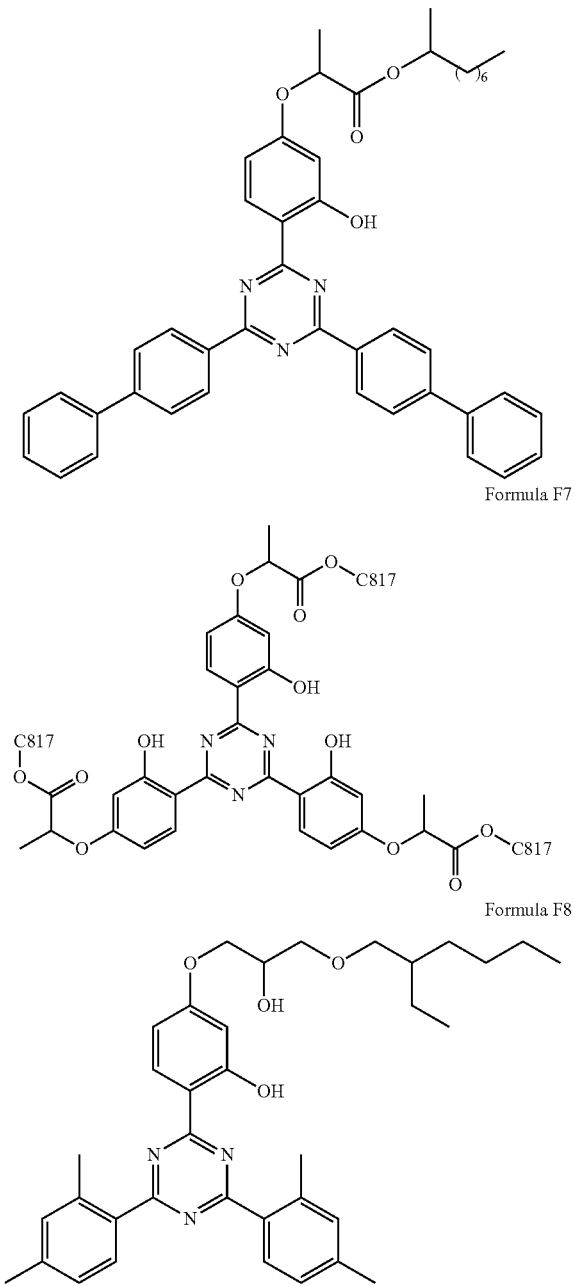

formula (A6a)

Formula F7

Formula F8

The advantages of the process of the presently claimed invention are,
i) the process is commercially viable and highly cost effective; and
ii) the process provides the final product without any colour imparting impurities.

EMBODIMENTS

In the following, there is provided a list of embodiments to further illustrate the present disclosure without intending to limit the disclosure to the specific embodiments listed below.

1. A process for preparing a compound of formula (A),

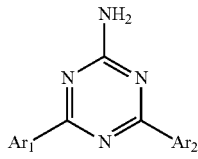

formula (A)

wherein $Ar_1$ and $Ar_2$ are independently a moiety of the formula (B),

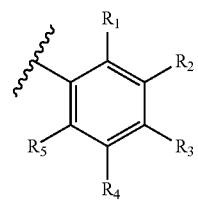

formula (B)

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of reacting at least one compound of formula (C)

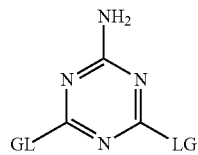

formula (C)

wherein LG is halogen, O—S(=O)$_2$CF$_3$ or O—S(=O)$_2$CH$_3$;

and at least one compound of formula (B2),

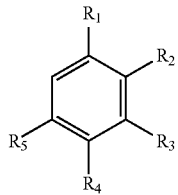

formula (B2)

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

in the presence of at least one acid.

2. The process according to embodiment 1, wherein the at least one acid is selected from the group consisting of inorganic acids, Lewis acids, and organic acids.

3. The process according to embodiment 2, wherein the inorganic acids are selected from the group consisting of sulfuric acid, hydrochloric acid, phosphoric acid, perchloric acid, nitric acid, nitrous acid, sulphurous acid, chloric acid, chlorous acid and hypochlorous acid.

4. The process according to embodiment 2, wherein the Lewis acids are selected from the group consisting of AsX$_3$, GaX$_3$, BX$_3$, BX$_3$—(C$_2$H$_5$)$_2$O, BX$_3$—S(CH$_3$)$_2$, AlX$_3$, (C$_2$H$_5$)$_2$AlX, SbX$_3$, SbX$_5$, SnX$_2$, MgX$_2$, MgX$_2$—O(C$_2$H$_5$)$_2$, ZnX$_2$, BiX$_3$, FeX$_2$, TiX$_2$, TiX$_4$, NbX$_5$, NiX$_2$, CoX$_2$, HgX$_2$, PbX$_2$, MnX$_2$, CuX, CuX$_2$ whereby X in each case denotes F, Cl, Br, CF$_3$—S(=O)$_2$O, CH$_3$—S(=O)$_2$O, or I; BH$_3$, B(CH$_3$)$_3$, GaH$_3$, AlH$_3$, Al(acetate)(OH)$_2$, Al[OCH(CH$_3$)$_2$]$_3$, Al(OCH$_3$)$_3$, Al(OC$_2$H$_5$)$_3$, Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$; Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$.

5. The process according to embodiment 4, wherein the at least one Lewis acid is selected from the group consisting of BX$_3$, BX$_3$—(C$_2$H$_5$)$_2$O, BX$_3$—S(CH$_3$)$_2$, AlX$_3$, ZnX$_2$, FeX$_3$ and TiX$_4$, whereby X in each case denotes F, Cl, or Br.

6. The process according to embodiment 2, wherein the organic acids are selected from the group consisting of organic carboxylic acid, organic phosphoric acid and organic sulfonic acid.

7. The process according to embodiment 1, wherein R$_1$, R$_2$, R$_3$, R$_4$ and R$_5$ are independently selected from the group consisting of hydrogen, halogen, substituted or unsubstituted, linear or branched C$_1$-C$_{24}$ alkyl, substituted or unsubstituted C$_6$-C$_{24}$ aryl, C(=O)R and OR, wherein R is selected from the group consisting of hydrogen, substituted or unsubstituted, linear or branched C$_1$-C$_{24}$ alkyl, substituted or unsubstituted, linear or branched C$_2$-C$_{24}$ alkenyl, substituted or unsubstituted C$_5$-C$_{24}$ cycloalkyl, substituted or unsubstituted C$_5$-C$_{24}$ cycloalkenyl, substituted or unsubstituted C$_6$-C$_{24}$ aryl and substituted or unsubstituted C$_7$-C$_{24}$ arylalkyl.

8. The process according to embodiment 1, wherein the molar ratio of the at least one acid to the at least one compound of formula (C) is in in the range of 1:10 to 10:1.

9. The process according to embodiment 1, wherein the molar ratio of the at least one compound of formula (B2) to the at least one compound of formula (C) is in the range of 1:1 to 5:2.

10. The process according to embodiment 1, wherein the at least one compound of formula (C) and the at least one compound of formula (B2) are reacted in the presence of at least one solvent selected from the group consisting of aliphatic hydrocarbons, aliphatic acyclic ether, aliphatic cyclic ether and carbon disulfide.

11. The process according to embodiment 10, wherein the molar concentration of the at least one compound of formula (C) in the at least one solvent is in the range of 0.5 M to 8.0 M.

12. The process according to embodiment 10, wherein the molar concentration of the at least one compound of formula (82) in the at least one solvent is in the range of 0.5 M to 8.0 M.

13. The process according to embodiment 10, wherein the aliphatic cyclic ether is dioxane.

14. The process according to embodiment 1, wherein the at least one compound of formula (C) and the at least one compound of formula (B2) are reacted at a temperature in the range of 0° C. to 250° C.

15. The process according to embodiment 1, wherein the at least one compound of formula (C) and the at least one compound of formula (82) are reacted for a period in the range of 30 minutes to 24 hours.

16. A process for preparing a compound of formula (D),

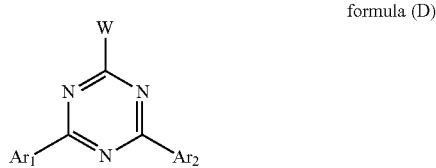

formula (D)

wherein Ar$_1$ and Ar$_2$ are defined as in embodiment 1, and W is selected from the group consisting of F, Cl, and Br, comprising at least the steps of
i) reacting a compound of formula (A) obtained according to one or more of embodiments 1 to 15 with at least one diazotizing reagent to obtain a diazonium salt of formula (Aa);

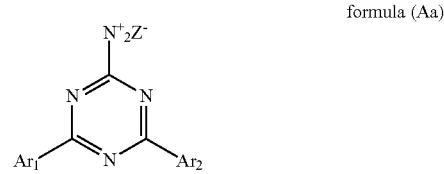

formula (Aa)

wherein Ar$_1$ and Ar$_2$ are as defined as in embodiment 1, and Z$^-$ is selected from the group consisting of BF$_4^-$, F$^-$, Cl$^-$ or Br$^-$; and
ii) reacting the diazonium salt of formula (Aa) obtained in step i) with at least one reagent of formula M(M$_a$)$_n$, wherein
M is selected from the group consisting of Cu, H and K,
M$_a$ is Cl, Br, I, BF$_4^-$ and
n is 1 to 4,
to obtain a compound of formula (D).

17. The process according to embodiment 16, wherein the at least one diazotizing reagent is selected from the group consisting of at least one alkyl nitrite and at least one compound of formula G(NO$_2$)$_o$ in combination with at least one acid;
wherein G is selected from the group consisting of Na, K, Li, Mg, Cs, Ba and
o is 1 to 2.

18. The process according to embodiment 16, wherein the at least one diazotizing reagent further comprises at least one chlorotrialkylsilane.

19. The process according to embodiment 16, wherein the at least one alkyl nitrite is selected from the group consisting of tert-butyl nitrite and isoamyl nitrite.

20. The process according to embodiment 18, wherein the at least one chlorotrialkylsilane is selected from the group consisting of chlorotrimethylsilane, chlorotriethylsilane and tert-butyl chlorodimethylsilane.

21. The process according to embodiment 17, wherein the at least one acid is selected from inorganic acids and organic acids.

22. The process according to embodiment 21, wherein the inorganic acids are selected from the group consisting of sulfuric acid, hydrochloric acid, phosphoric acid, perchloric acid, nitric acid, nitrous acid, sulphurous acid, chloric acid, chlorous acid and hypochlorous acid.

23. The process according to embodiment 21, wherein the organic acids are selected from the group consisting of carboxylic acids and sulfonic acids.

24. The process according to embodiment 23, wherein the carboxylic acids are selected from the group consisting of lactic acid, acetic acid, formic acid, citric acid, oxalic acid, uric acid and malic acid.

25. The process according to embodiment 23, wherein the sulfonic acids are selected from the group consisting of methane sulfonic acid, trifluoromethane sulfonic acid, trichloromethane sulfonic acid and p-toluene sulfonic acid.

26. The process according to embodiment 16, wherein step i) is carried out at a temperature in the range of 0 to 220° C.

27. The process according to embodiment 16, wherein step i) is carried out in the presence of at least one solvent selected from the group consisting of aliphatic and aromatic hydrocarbons, halogenated aliphatic and aromatic hydrocarbons, ethers and carbon disulfide.

28. The process according to embodiment 16, wherein the weight ratio of the diazotizing agent to the at least one compound of formula (A) is in the range of 1:1 to 10:1.

29. The process according to embodiment 16, wherein step i) is carried out for a period of 30 minutes to 24 hours.

30. The process according to embodiment 16, wherein the at least one reagent of formula $M(M_a)_n$ is selected from the group consisting of CuT, HT, KI and $BF_4^-$, wherein T is selected from CN, F, Cl and Br; and n is 1 to 4.

31. The process according to embodiment 16, wherein step ii) is carried out at a temperature in the range of 0 to 200° C.

32. The process according to embodiment 16, wherein the weight ratio of the at least one reagent of formula $M(M_a)_n$ to the at least one compound of formula (Aa) is in the range of 1:1 to 10:1.

33. The process according to embodiment 16, wherein step ii) is carried out for a period of 30 minutes to 24 hours.

34. A process for preparing a compound of formula (F),

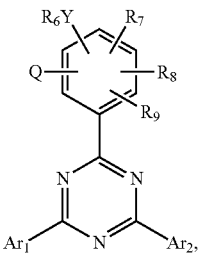

formula (F)

wherein $Ar_1$ and $Ar_2$ are the same or different and are as defined as in embodiment 1, Q is selected from hydrogen and OH;

$R_5$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is selected from the group consisting of hydrogen, halogen, O, —NR", or S, wherein R" is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present, comprising at least the steps of reacting at least one compound of formula (D) obtained according to one or more of embodiments 16 to 33,

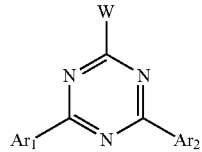

formula (D)

wherein W is halogen, $Ar_1$ and $Ar_2$ are the same or different and are as defined as in embodiment 1, and at least one compound of formula (E),

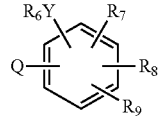

formula (E)

wherein

Q is selected from hydrogen and OH;

$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR, R and R' are not both hydrogen, and Y is selected from the group consisting of hydrogen, halogen, O, —NR", or S, wherein R" is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present, in the presence of an at least one acid.

35. The process according to embodiment 34, wherein the at least one acid is a Lewis acid selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I;

$BH_3$, $B(CH_3)_3$, $GaH_3$, $AlH_3$, Al(acetate)(OH)$_2$, Al[OCH$(CH_3)_2$]$_3$, Al(OCH$_3$)$_3$, Al(OC$_2$H$_5$)$_3$, Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$; Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$.

36. The process according to embodiment 35, wherein the at least one Lewis acid is selected from the group consisting of $BX_3$, $BX_3$—$(C_2H_5)_2O$, $BX_3$—$S(CH_3)_2$, $AlX_3$, $ZnX_2$ and $TiX_4$, whereby X in each case denotes F, Cl, or Br.

37. The process according to embodiment 34, wherein the molar ratio of the at least one acid to the at least one compound of formula (D) is in in the range of 1:10 to 10:1.

38. The process according to embodiment 34, wherein the molar ratio of the at least one acid to the at least one compound of formula (E) is in in the range of 1:10 to 10:1.

39. The process according to embodiment 34, wherein the molar ration of the at least one compound of formula (D) to the at least one compound of formula (E) is in in the range of 2:5 to 5:2.

40. The process according to embodiment-34, wherein the at least one compound of formula (D) and the at least one compound of formula (E) are reacted in presence of at least one solvent selected from the group consisting of aliphatic and aromatic hydrocarbons, halogenated aliphatic, halogenated aromatic hydrocarbons, ethers and carbon disulphide.

41. The process according to embodiment 40, wherein the aliphatic cyclic ether is dioxane.

42. The process according to embodiment 34, wherein the reaction is carried out at a temperature in the range of 0 to 250° C.

43. The process according to embodiment 34, wherein the at least one compound of formula (E) and the at least one compound of formula (D) are reacted for a period of 30 minutes to 24 hours.

While the presently claimed invention has been described in terms of its specific embodiments, certain modifications and equivalents will be apparent to those skilled in the art and are intended to be included within the scope of the presently claimed invention

EXAMPLES

The presently claimed invention is illustrated in detail by non-restrictive working examples which follow. More particularly, the test methods specified hereinafter are part of the general disclosure of the application and are not restricted to the specific working examples.

General Procedure for Synthesis of Compound of Formula (A)

To a solution of compound of formula C (1 mol) in 1,2-dichlorobenzene was added at least one acid (3 mol) in one portion and heated to 50° C. to obtain a mixture. To this mixture, a solution of compound of formula B2 (2.08 mol) in 1,2-dichlorobenzene was added at 80° C. After completion of addition of the compound of formula B2, the temperature was raised to 110° C. and the reaction was stirred for 3 hrs. The hot reaction mass was quenched by adding to ice-cold water. The product was precipitated out as yellow solid and was filtered. The yellow solid was taken in heptane (50 mL) and stirred for 1 hr, filtered and dried to obtain the pure product.

Example 1: Synthesis of 4,6-bis(4-phenylphenyl)-1,3,5-triazin-2-amine

To a solution of 10 g (61 mmol) of 2,4-dichlirotriazin-6-amine in 1,2-dichlorobenzene (50 ml) was added 24.4 g (183 mmol) of AlCl$_3$ in one portion and heated to 50° C. to obtain a dark suspension. To this suspension, a solution of 19.6 g (127 mmol) of biphenyl in 1,2-dichlorobenzene (40 ml) was added at 80° C. After completion of addition, the temperature was raised to 110° C. and the reaction was stirred for 3 hrs. The hot reaction mass was quenched by adding to ice-cold water. The product was precipitated out as yellow solid and was filtered. The yellow solid was taken in heptane (50 mL) and stirred for 1 hr, filtered and dried to obtain the pure product (20.8 g; 87%).

General Procedure for Synthesis of Compound of Formula (D)

Charged the diazotization reagent (1.5 mmol) to dioxane (2 mL) to obtain a solution. The above solution was cooled to 15-20° C. To this solution slowly added a compound of formula (A, 1.25 mmol). After completion of addition of the compound of formula (A), the reaction temperature was raised to 60° C. and maintained at this temperature for 2 hrs. Upon completion, the reaction was quenched by adding water and the product was extracted using dichloromethane. The organic layer was separated and concentrated under vacuum to obtain the desired product.

Example 2: Synthesis of 2-chloro-4,6-bis(4-phenylphenyl)-1,3,5-triazine

Charged t-butyl nitrite (1.5 mmol) and trimethyl silyl chloride (1.5 mmol) to dioxane at room temperature to obtain a solution. The above solution was cooled to 15-20° C. To this solution slowly added 4,6-bis(4-phenylphenyl)-1,3,5-triazin-2-amine 3 (Example 1, 0.5 g, 1.25 mmol in 6 ml of Dioxane). After completion of addition of compound of formula (Al), the reaction temperature was raised to 60° C. and maintained the temperature at 60° C. for 2 hrs. On completion, the reaction was quenched by adding water and the product was extracted using dichloromethane. The organic layer was separated and concentrated under vacuum to obtain the desired product as light yellow solid (70%).

General Procedure for Synthesis of Compound of Formula (F)

To a solution of compound of formula D (1 mol) in 1,2-dichlorobenzene was added at least one acid (3 mol) in one portion and heated to 50° C. to obtain a mixture. To this mixture, a solution of compound of formula E (1.08 mol) in 1,2-dichlorobenzene was added at 80° C. After completion of addition of compound of formula E, the temperature was raised to 110° C. and the reaction was stirred for 3 hrs. The hot reaction mass was quenched by adding to ice-cold water. The product was precipitated out and was filtered. The solid product was purified and dried to obtain the pure product.

The invention claimed is:
1. A process for preparing a compound of formula (A):

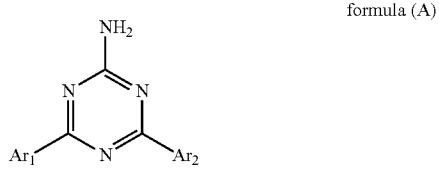

formula (A)

wherein $Ar_1$ and $Ar_2$ are independently a moiety of the formula (B):

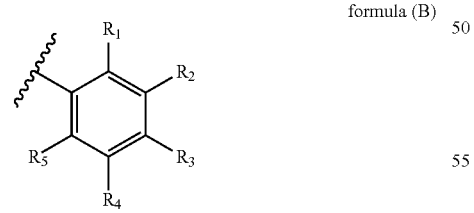

formula (B)

wherein
$R_1$, $R_2$, $R_3$, R and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and
R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;
comprising at least the steps of reacting at least one compound of formula (C)

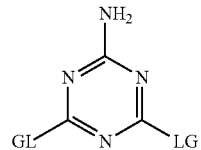

formula (C)

wherein LG is halogen, O—S(=O)$_2$CF$_3$ or O—S(=O)$_2$CH$_3$;
and at least one compound of formula (B2)

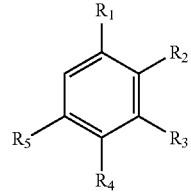

formula (B2)

wherein
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

in the presence of at least one acid.

2. The process according to claim 1, wherein the at least one acid is selected from the group consisting of inorganic acids, Lewis acids, and organic acids.

3. The process according to claim 2, wherein the Lewis acids are selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, $Li(acetate)$, $Zr(acetylacetonate)_4$, $Si(acetate)_4$, $K(acetate)$, $Na(acetate)$, $Cs(acetate)$, $Rb(acetate)$, $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, $Ag(acetate)$, $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri-fluoromethanesulfonate)_2$ and $Cu(tosylate)_2$.

4. The process according to claim 3, wherein the at least one Lewis acid is selected from the group consisting of $BX_3$, $BX_3$—$(C_2H_5)_2O$, $BX_3$—$S(CH_3)_2$, $AlX_3$, $ZnX_2$, $FeX_3$ and $TiX_4$, whereby X in each case denotes F, Cl, or Br.

5. The process according to claim 1, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, C(=O)R and OR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

6. The process according to claim 1, wherein the molar ratio of the at least one acid to the at least one compound of formula (C) is in the range of 1:10 to 10:1.

7. The process according to claim 1, wherein the molar ratio of the at least one compound of formula (B2) to the at least one compound of formula (C) is in the range of 1:1 to 5:2.

8. The process according to claim 1, wherein the at least one compound of formula (C) and the at least one compound of formula (B2) are reacted in the presence of at least one solvent selected from the group consisting of aliphatic hydrocarbons, aliphatic acyclic ether, aliphatic cyclic ether and carbon disulfide.

9. The process according to claim 8, wherein the molar concentration of the at least one compound of formula (C) in the at least one solvent is in the range of 0.5 M to 8.0 M.

10. The process according to claim 8, wherein the molar concentration of the at least one compound of formula (B2) in the at least one solvent is in the range of 0.5 M to 8.0 M.

11. The process according to claim 8, wherein the aliphatic cyclic ether is dioxane.

12. A process for preparing a compound of formula (D),

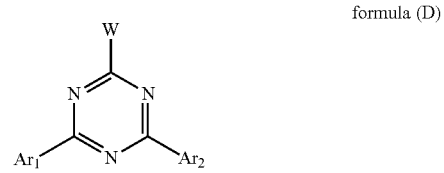

formula (D)

wherein $Ar_1$ and $Ar_2$ are defined as in claim 1, and
W is selected from the group consisting of F, Cl, and Br, comprising at least the steps of
i) reacting a compound of formula (A) obtained according to claim 1 with at least one diazotizing reagent to obtain a diazonium salt of formula (Aa);

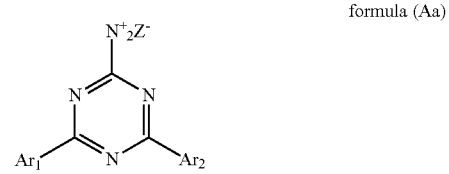

formula (Aa)

wherein $Ar_1$ and $Ar_2$ are as defined as in claim 1, and Z is selected from the group consisting of $BF_4^-$, $F^-$, $Cl^-$ or $Br^-$; and
ii) reacting the diazonium salt of formula (Aa) obtained in step i) with at least one reagent of formula $M(M_a)_n$, wherein
M is selected from the group consisting of Cu, H and K,
$M_a$ is Cl, Br, I, $BF_4^-$ and
n is 1 to 4,
to obtain a compound of formula (D).

13. A process for preparing a compound of formula (F)

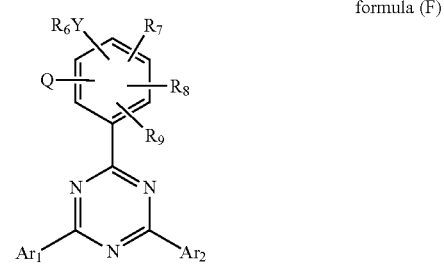

formula (F)

wherein $Ar_1$ and $Ar_2$ are the same or different and are as defined as in claim 1,
Q is selected from hydrogen and OH;
$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OCOR, CN, SR, S(=O)$_2$R, S(=O)$_2$OH and S(=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is selected from the group consisting of hydrogen, halogen, O, —NR'', or S, wherein R'' is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_6$-$C_{24}$ cycloalkyl and substituted or unsubstituted $C_5$-$C_{24}$ cycloalkenyl; with the proviso that in case Y is hydrogen or halogen, then $R_6$ is not present, comprising at least the steps of reacting at least one compound of formula (D),

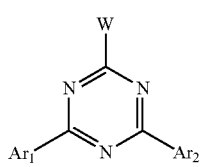

formula (D)

wherein W is halogen, $Ar_1$ and $Ar_2$ are the same or different and are as defined as in claim 1, wherein the compound of formula (D) is obtained from a diazonium salt of formula (Aa),

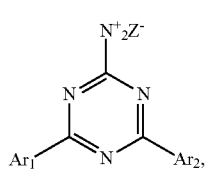

formula (Aa)

wherein Z is selected from the group consisting of $BF_4^-$, $F^-$, $Cl^-$ or $Br^-$;

and at least one compound of formula (E),

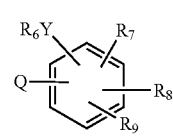

formula (E)

wherein

Q is selected from hydrogen and OH;

$R_6$ is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR, OCOR, CN, SR, S(=O)$_2$R, S(=O)$_2$OH and S=O)$_2$OM, wherein M is an alkali metal, R and R' are independently selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen, and Y is selected from the group consisting of hydrogen, halogen, O, —NR'', or S, wherein R'' is selected from the group consisting of hydrogen, substituted or unsubstituted linear or branched $C_1$-$C_{24}$ alkyl, substituted or unsubstituted linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present, in the presence of an at least one acid.

14. The process according to claim 13, wherein the at least one acid is a Lewis acid selected from the group consisting of $AsX_3$, $GaX_3$, $BX_3$, $BX_3$—$(C_2H_5)_2O$, $BX_3$—$S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, CuX, $CuX_2$ whereby X in each case denotes F, Cl, Br, $CF_3$—S(=O)$_2$O, $CH_3$—S(=O)$_2$O, or I;

$BH_3$, $B(CH_3)_3$, $GaH_3$, $AlH_3$, Al(acetate)(OH)$_2$, Al[OCH(CH$_3$)$_2$]$_3$, Al(OCH$_3$)$_3$, Al(OC$_2$H$_5$)$_3$, Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$; Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Ti(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$.

15. The process according to claim 14, wherein the at least one Lewis acid is selected from the group consisting of BX$_3$, BX$_3$—(C$_2$H$_5$)$_2$O, BX$_3$—S(CH$_3$)$_2$, AlX$_3$, ZnX$_2$ and TiX$_4$, whereby X in each case denotes F, Cl, or Br.

* * * * *